(12) United States Patent
Han et al.

(10) Patent No.: US 10,774,107 B2
(45) Date of Patent: *Sep. 15, 2020

(54) DNA GRIDIRON COMPOSITIONS AND METHODS

(71) Applicant: ARIZONA BOARD OF REGENTS ON BEHALF OF ARIZONA STATE UNIVERSITY, Scottsdale, AZ (US)

(72) Inventors: Dongran Han, Cambridge, MA (US); Hao Yan, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/202,841

(22) Filed: Nov. 28, 2018

(65) Prior Publication Data
US 2019/0144491 A1 May 16, 2019

Related U.S. Application Data

(63) Continuation of application No. 15/121,007, filed as application No. PCT/US2015/017553 on Feb. 25, 2015, now Pat. No. 10,189,874.

(60) Provisional application No. 61/944,677, filed on Feb. 26, 2014.

(51) Int. Cl.
*C07H 21/04* (2006.01)
*C07H 1/00* (2006.01)

(52) U.S. Cl.
CPC ............... *C07H 21/04* (2013.01); *C07H 1/00* (2013.01)

(58) Field of Classification Search
CPC .... C07H 1/00; C07H 21/04; C12Q 2600/178; C12N 15/11; C12N 2330/30
USPC ............ 435/6.1, 91.1, 91.31; 536/23.1, 24.5
See application file for complete search history.

(56) References Cited

U.S. PATENT DOCUMENTS

| | | | |
|---|---|---|---|
| 4,469,863 A | 9/1984 | Ts'o et al. | |
| 4,559,157 A | 12/1985 | Smith et al. | |
| 4,608,392 A | 8/1986 | Jacquet et al. | |
| 4,612,302 A | 9/1986 | Szabo et al. | |
| 4,684,620 A | 8/1987 | Hruby et al. | |

(Continued)

FOREIGN PATENT DOCUMENTS

| WO | WO2010060030 A1 | 5/2010 |
|---|---|---|
| WO | WO2013119676 A1 | 8/2013 |

OTHER PUBLICATIONS

Agrawal et al., (1988). "Oligodeoxynucleoside phophoramidates and phosphorrothioates as inhibitors of human immunodeficiency virus." Proc. Natl. Acad. Sci. 85: 7079-7083.

(Continued)

*Primary Examiner* — Jane J Zara
(74) *Attorney, Agent, or Firm* — Duane Morris LLP

(57) ABSTRACT

Novel compositions and methods for engineering wireframe architectures and scaffolds of increasing complexity by creating gridiron-like DNA structures (FIG. 1). A series of four-arm junctions are used as vertices within a network of double-helical DNA fragments. Deliberate distortion of the junctions from their most relaxed conformations ensures that a scaffold strand can traverse through individual vertices in multiple directions. DNA gridirons, ranging from two-dimensional arrays with reconfigurability to multilayer and three-dimensional structures and curved objects, can be assembled according the methods presented herein.

8 Claims, 5 Drawing Sheets
(1 of 5 Drawing Sheet(s) Filed in Color)
Specification includes a Sequence Listing.

(56) References Cited

U.S. PATENT DOCUMENTS

| | | | |
|---|---|---|---|
| 4,816,567 | A | 3/1989 | Cabilly et al. |
| 4,820,508 | A | 4/1989 | Wortzman |
| 4,853,371 | A | 8/1989 | Coy et al. |
| 4,873,192 | A | 10/1989 | Kunkel |
| 4,938,949 | A | 7/1990 | Borch et al. |
| 5,023,243 | A | 1/1991 | Tullis |
| 4,992,478 | A | 2/1991 | Geria |
| 6,239,116 | B1 | 5/2001 | Krieg et al. |
| 2007/0082352 | A1 | 4/2007 | Cumpson |
| 2008/0124366 | A1 | 5/2008 | Ohlfest et al. |
| 2011/0275702 | A1 | 11/2011 | Chang et al. |
| 2012/0190732 | A1 | 7/2012 | Chang et al. |
| 2015/0004193 | A1 | 1/2015 | Chang et al. |

OTHER PUBLICATIONS

Agrawal et al., (1992). "Antisense oligonucleotides as antiviral agents." Trends in Biotechnology 10: 152-158.

Bachmann et al., (2010). "Vaccine delivery: a matter of size, geometry, kinetics and molecular patterns." Natural Reviews Immunology 10:787-796.

Ballas et al., (1996). "Induction of NK Activity in Murine and Human Cells by CpG Motifs in Oligodeoxynucleotides and Bacterial DNA." J. Immunol. 157(5): 1840-1845.

Beaucage et al., (1981). "Deoxynucleoside Phosphoramidites—A New Class of Key Intermediates for Deoxypolynucleotide Synthesis." Tetrahedron Letters 22(20): 1859-1862.

Bode et al., (2011). "CpG DNA as a vaccine adjuvant." Expert Rev. Vaccines 10(4): 499-511.

Burton, (2010). "Scaffolding to build a rational vaccine design strategy." PNAS 107(42): 17859-17860.

Cao and Chen, "Characterization of Antibody Responses Against the 2F5 Epitope ELDKWA Using HIV-1 Env-Mediated Membrane Fusion and Neutralization Assays." Tsinghua Science and Technology, 2010; 15(4): 447-451.

Clackson et al., (1991). "Making antibody fragments using phage display libraries." Nature 352: 624-628.

Cowdrey et al., (1996). "Bacterial DNA Induces NK Cells to Produce IFN-gamma In Vivo and Increases the Toxicity of Lipopolysaccharides." The Journal of Immunology 156(12): 4570-4575.

Dayhoff et al., (1978). "A Model of Evolutionary Change in Proteins." Atlas of Protein Sequence and Structure 345-352.

Dietz H. et al., "Folding DNA into Twisted and Curved Nanoscale Shapes", Science 325(5941), 725-730 (2009).

Douglas S. et al., "Self-assembly of DNA into nanoscale three-dimensional shapes", Nature 459, 414-418 (2009).

Elgueta et al., (2010). "The immortality of humeral immunity." Immunological Reviews 236: 139-150.

Froehler et al., (1986). "Deoxyncleoside H-Phosphonate diester intermediates in the synthesis of internucleotide phosphate analogues." Tetrahedron Letters 27(46): 5575-5578.

Froehler et al., (1986). "Synthesis of DNA via deoxynucleoside H-phosphonate intermediates." Nucleic Acids Research 14(13): 5399-5407.

Fu T. et al., "DNA Double-Crossover Molecules", Biochemistry 32(13), 3211-3220 (1993).

Gaffney et al., (1988). "Large-scale oligonucleotide synthesis by the H-phosphonate method." Tetrahedron Letters 29(22): 2619-2622.

Garegg et al., (1986). "Nucleoside H-Phosphonates. III. Chemical synthesis of oligodeoxyribonucleotides by the hydrogenphophonate approach." Tetrahedron Letters 27(34): 4051-4054.

Garegg et al., (1986). "Nucleoside H-phosphonates. IV. Automated solid phase synthesis of oligoribonucleotides by the hydrogenphosphonate approach." Tetrahedron Letters 27(34): 4055-4058.

Gietl A. et al., "DNA origami as biocompatible surface to match single-molecule and ensemble experiments", Nucleic Acids Res 40(14), e110 (2012), 10 pages.

Goodchild (1990). "Conjugates of oligonucleotides and modified oligonucleotides: a review of their synthesis and properties." Bioconjugate Chemistry 1 (3): 165-187.

Han D. et al., "DNA gridiron nanostructures based on four-arm junctions", Science 339(6126), 1412-1415 (2013).

Han et al., (2011). "DNA Origami with Complex Curvatures in Three-Dimensional Space." Science 332(6027): 342-346.

He et al., (2008). "Hierarchical self-assembly of DNA into symmetric supramolecular polyhedral." Nature 452: 198-202.

Hosmalin et al. Priming With T Helper Cell Epitope Peptides Enhances the Antibody Response to the Envelope Glycoprotein of HIV-1 in Primates. J. Immunol. 1991; 146(5): 1667-1673.

Jerala M. et al., "A DNA Origami of Slovenia in Nano Dimensions", Acta Chim Slav 58(1), 181-184 (2011).

Ke et al., (2008). "Self-Assembled Water-Soluble Nucleic Acid Probe Tiles for Label-Free RNA Hybridization Assays." Science 319: 180-183.

Kohler et al., (1975). "Continuous cultures of fused cells secreting antibody of predefined specificity." Nature 256:495-497.

Krieg et al., (1995). "CpG motifs in bacterial DNA trigger direct B-cell activation." Nature 374(6522): 546-549.

Kunkel et al., (1987). "Rapid and efficient site-specific mutagenesis without phenotypic selection." Methods in Enzymology 154: 367-382.

Kunkel, (1985). "Rapid and efficient site-specific mutagenesis without phenotypic selection." Proc. Natl. Acad. Sci. 82: 488-492.

Kutsch et al., (2002). "Direct and Quantitative Single-Cell Analysis of Human Immunodeficiency Virus Type 1 Reactivation from Latency." J Viral. 76(17): 8776-8786.

Li et al., (2011). "Self-Assembled Multivalent DNA Nanostructures for Noninvasive Intracellular Delivery of Immunostimulator CpG Oligonucleotides." ACS Nano 5(11): 8783-8789.

Liu et al., (2011). "Targeted Cell-Cell Interactions by DNA Nanoscaffold-Templated Multivalent Bispecific Aptamers." Small 7(12): 1673-1682.

Liu et al., (2012). "A DNA Nanostructure Platform for Directed Assembly of Synthetic Vaccines." Nano Letters 12: 4254-4259.

Lu et al., (2010). "Polyvalent AIDS Vaccines." Current HIV Research 8(8): 622-629.

Mao C. et al., "Designed Two-Dimensional DNA Holliday Junction Arrays Visualized by Atomic Force Microscopy", J l\m Chem Soc 121(23), 5437-5443 (1999).

Marini M. et al., "A Revertible, Autonomous, Self-Assembled DNA-Origami Nanoactuator", Nano Lett 11(12), 5449-5454 (2011).

Marks et al., (1991). "By-passing immunization: Human antibodies from V-gene libraries displayed on phage." Journal of Molecular Biology 222(3): 581-597.

Marks et al., (1992). "By-Passing Immunization: Building High Affinity Human Antibodies by Chain Shuffling." Bio/ Technology 10: 779-783.

McCafferty et al., (1990). "Phage antibodies: filamentous phage displaying antibody variable domains." Nature 348: 552-554.

McElrath et al., (2010) "Induction of Immunity to Human Immunodeficiency Virus Type-1 by Vaccination." Immunity 33(4): 542-554.

McGhee et al., (1993). "New Perspectives in Mucosal Immunity With Emphasis on Vaccine Development," Sem. Hematol., 30(4): 3-15.

McKinney S. et al., "Structural dynamics of individual Holliday junctions", Nature Struct Biol 10(2), 93-97 (2002).

Miick S. et al., "Crossover isomer bias is the primary sequence-dependent property of immobilized Holliday junctions" Proc Nall Acad Sci USA 94(17), 9080-9084 (1997).

Morrison et al., (1984). "Chimeric human antibody molecules: Mouse antigen-binding domains with human constant region domains." Proc. Natl. Acad. Sci. 81: 6851-6855.

Moses et al., (2007). "The growing applications of click chemistry." Chem. Soc. Rev. 2007 36(8): 1249-62.

Mouquet et al., (2010). "Polyreactivity increases the apparent affinity of anti-HIV antibodies by heteroligation." Nature 467: 591-596.

Ofek et al., (2010). "Elicitation of Structure-Specific Antibodies by Epitope Scaffolds." PNAS 107(42): 17880-17887.

(56) References Cited

OTHER PUBLICATIONS

Patent Cooperation Treaty, International Search Authority, Search Report and Written Opinion for PCT/US15/17553, 16 pages, dated Jun. 17, 2015.
Patent Cooperation Treaty, International Searching Authority, Search Report and Written Opinion for PCT/ US2013/24945, 9 pages, dated May 20, 2013.
Roberts et al., (2011). "B cells do not take up bacterial DNA: an essential role for antigen in exposure of DNA to toll-like receptor-9" Immunology & Cell Biology 89(4): 517-525.
Rostovtsev et al., (2002). "A Stepwise Huisgen Cycloaddition Process: Copper (1)-Catalyzed Regioselective 'Ligation' of Azides and Terminal Alkynes." Angew. Chem. Int. Ed. 41(14): 2596-2599.
Rothemund W., "Folding DNA to create nanoscale shapes and patterns", Nature 440, 297-302 (2006).
Seeman N., "Nanomaterials Based on DNA", Annu Rev Biochem 79, 65-87 (2010).
Seeman, (2003). "At the Crossroads of Chemistry, Biology, and Materials: Structural DNA Nanotechnology." Chemistry & Biology 10: 1151-1159.
Uhlmann et al., (1990). "Antisense Oligonucleotides: A New Therapeutic Principle." Chemical Reviews 90(4).
Van Duyne et al., (2009). "The utilization of humanized mouse models for the study of human retroviral infections." Retrovirology 6: 76.
Waterhouse et al., (1993). "Combinatorial infection and in vivo recombination: a strategy for making large phage antibody repertoires." Nucleic Acids Research 21 (9): 2265-2266.
Zhang et al., (2010). "Exterior Modification of a DNA Tetrahedron." Chem Commun. 46: 6792-6794.
Zhao et al., (2010). "A Route to Scale up DNA Origami using DNA Tiles as Folding Staples." Angew. Chem. Int. Ed. 49: 1414-1417.
Zhao Z et al., "Organizing DNA Origami Tiles Into Larger Structures Using Preformed Scaffold Frames", Nano Lett 11 (7), 2997-3002 (2011).
Zolla-Pazner "Identifying Epitopes of HIV-1 That Induce Protective Antibodies". Nat. Rev. lmmunol. 2004; 4:199-210.
Zolnik et al. "Minireview: Nanoparticles and the Immune System." Endocrinol. 2010; 151 (2): 458-465.

DNA GRIDIRON COMPOSITIONS AND METHODS

CROSS-REFERENCE TO RELATED APPLICATIONS

This application is a continuation of U.S. patent application Ser. No. 15/121,007, filed on Aug. 23, 2016, which is a national stage entry of International Patent Application No. PCT/US2015/017553, filed on Feb. 25, 2015, which claims priority to U.S. Provisional Patent Application No. 61/944,677 filed on Feb. 26, 2014.

STATEMENT OF GOVERNMENT RIGHTS

This invention was made with government support under N000140911118 awarded by the Office of Naval Research, 1104373 awarded by the National Science Foundation, and W911NF-11-1-0137 awarded by the Army Research Office. The government has certain rights in the invention.

FIELD OF THE INVENTION

This disclosure relates to the field of nanotechnology and more particularly to the engineering of wireframe architectures and scaffolds using DNA structures.

BACKGROUND OF THE INVENTION

Self-assembling nucleic acid molecules have shown merit as versatile materials for organizing and constructing complex nano-scale structures. Methods are known for generation of complex DNA origami nanostructures with addressable surface features. For example, a long scaffold strand, most often the 7429-nucleotide (nt) circular genome of the M13mp18 bacteriophage, is organized and folded by interactions with a large number of short, synthetic, staple strands. The path of the scaffold strand in this approach has been restricted to discrete domains of parallel lines because it is based on the double crossover unit motif to link adjacent helices.

Because engineering wireframe architectures and scaffolds of increasing complexity is an important challenge in nanotechology, methods and compositions for achieving same are very useful and inventive.

SUMMARY OF THE INVENTION

We present a design strategy that uses an unusual set of immobile Holliday junction analogs (four-arm junctions) as the basic structural unit of DNA origami nanostructures and as joints to construct a variety of two-dimensional (2D) and 3D gridiron structures, in which the scaffold strand and corresponding double helices are not restricted to a 1D parallel, raster-fill pattern. By programming the connection between individual joints with DNA segments of variable lengths, we constructed complex wireframe geometries.

These and other aspects of the invention will be apparent upon reference to the following detailed description and figures. To that end, any patent and other documents cited herein are hereby incorporated by reference in their entirety.

BRIEF DESCRIPTION OF THE FIGURES

The patent application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Although intuitively one could imagine threading a single-stranded scaffold through a number of four-arm junction units in both horizontal and vertical directions to create gridiron like patterns, the structural properties of traditional Holliday junction impose certain challenges that require unconventional rearrangement of the junction unit conformation, as revealed by the design principles described below.

We compared a gridiron unit to a double crossover motif (FIG. 1A), and the DNA strands are abstracted to display only their polarity with the arrows pointing from 5' to 3'. In the gridiron unit, four four-arm junctions are linked together to form a two-layer square frame in which the helices on opposite sides lie in the same plane. An antiparallel arrangement between opposite sides of the square frame permits a single, central strand to traverse each of the helices.

Figure 1:
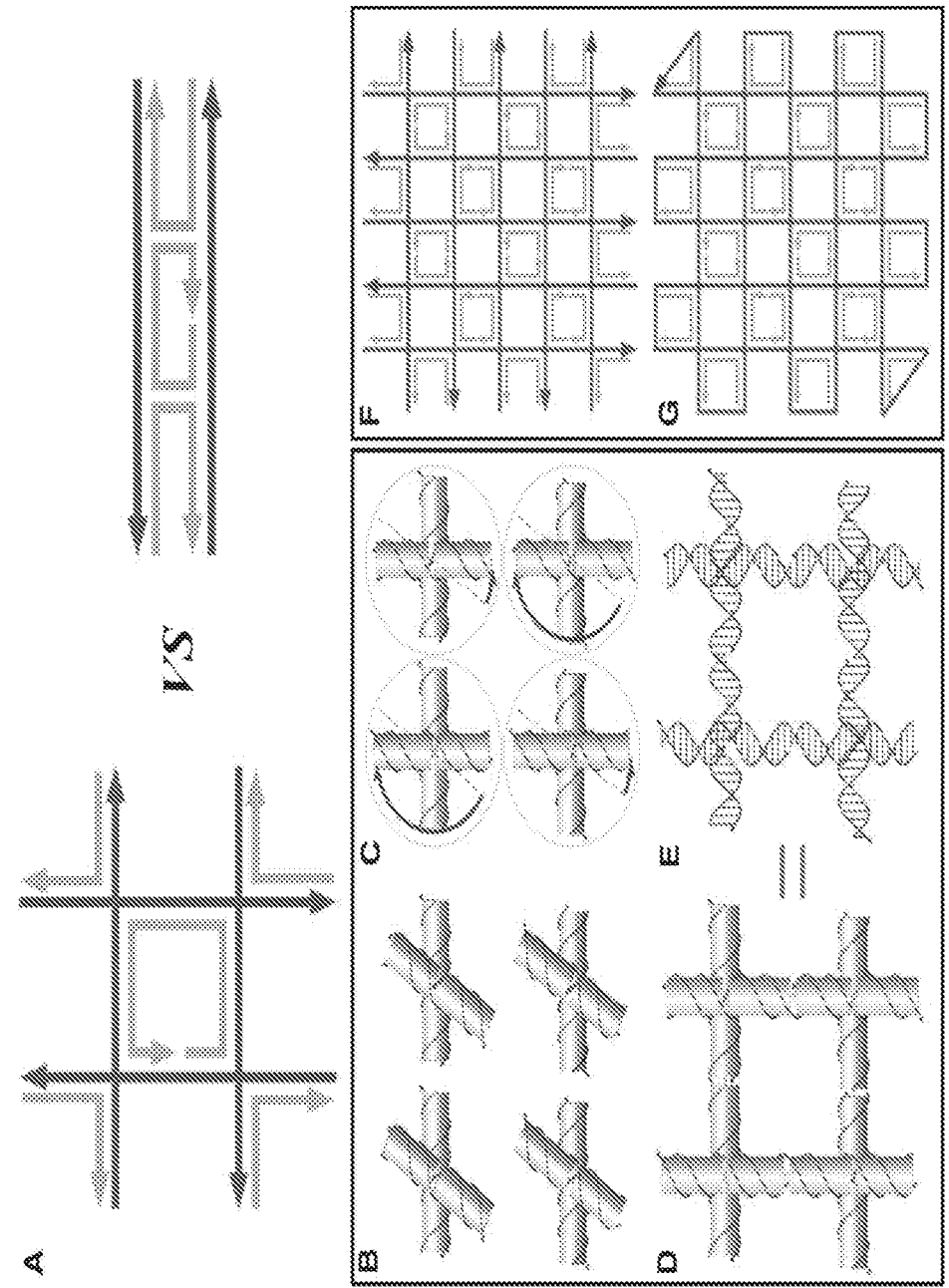
FIG. 1. (A) (Left) Geometry and strand polarity of a single gridiron unit formed from four four-arm junctions. (Right) Geometry and polarity of a double-crossover molecule motif used in conventional DNA origami structures. For both structures, the ssDNAs depicted in red are components of DNA double helices that serve as the scaffold strands. The ssDNA depicted in gray represents staple strands. (B) Models of four four-arm junction molecules in their relaxed conformation. The orientation of the upper two junctions differs from that of the lower two by a 180° in-plane rotation. Thus, the polarities of the continuous red strands in the upper and lower layers of the horizontally oriented helices are antiparallel to one another. (C) Models illustrating the deviation from a relaxed conformation required of the four individual junctions to form a gridiron unit. The blue arrows indicate that the top helix of the junctions in the upper-left and lower-right corners must be rotated ~150° clockwise, whereas in the upper-right and lower-left junctions they must be rotated ~30° counterclockwise. (D and E) Helical models illustrating a complete gridiron unit. (F and G) Schematics illustrating a typical scaffold-folding path for a 2D DNA gridiron pattern.

Each of the four junctions is depicted in its relaxed conformation (FIG. 1B) such that the helices form a right-handed twist with a 60° torsion angle. Deviation from a relaxed conformation is required of each junction to form the gridiron unit cell. First, the red strands in the horizontally oriented helices (both top and bottom images) can be linked together to produce continuous strands without reversing the 5'-to-3' polarity (FIGS. 1, B and C). Next, the vertically oriented helices need to be rotated in the plane about the junction points (FIG. 1C) to allow the formation of continuous 5'-to-3' connections between upper and lower junctions (FIGS. 1, D and E).

Connecting a number of gridiron units leads to the formation of a variety of 2D lattices (FIGS. 1, F and G). The red lines represent the DNA strands that are expected to retain an unperturbed helical structure with continuous base stacking. Meanwhile, the short strands (in gray) form the crossovers between helical domains and function as staples. A long scaffold strand is created by connecting the termini of the red strands with short single-stranded DNA (ssDNA) loops. In the most basic design, the scaffold begins at one corner, fills the first layer, changes direction at the opposite corner, and then fills the second layer to produce a structure in which the helices within the two layers are oriented perpendicularly with respect to each other. Lastly, the scaffold returns to its initial position to form a closed loop (FIG. 1G).

Figure 2:
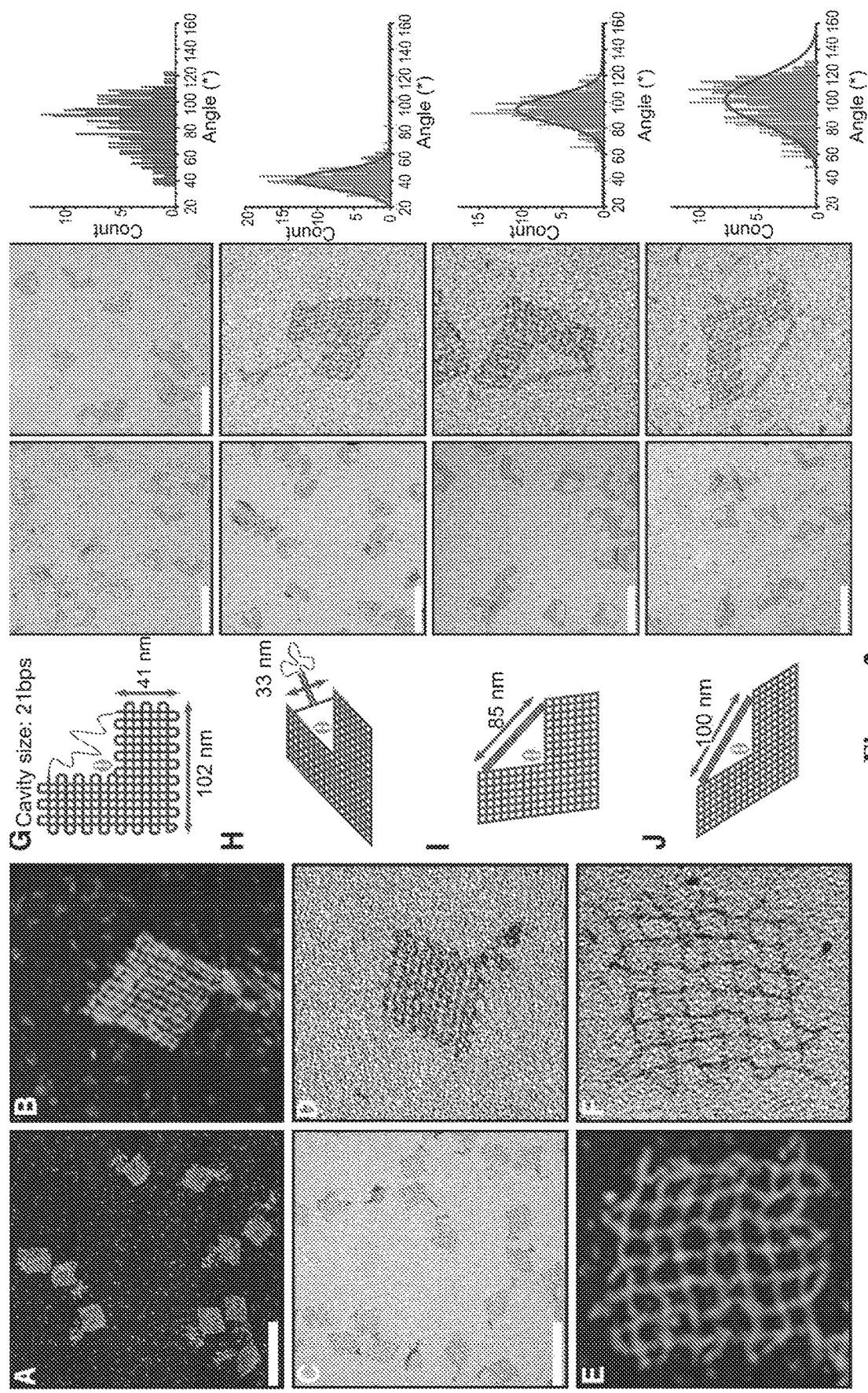
FIG. 2. (A to D) Images for a 2D gridiron structures with 21-bp cavities with AFM [(A) and (B)] and TEM images [(C) and (D)]. (E and F) Images for a 2D gridiron with 63-bp cavities with AFM (E) and TEM images (F). (G to J) Schematics (left), TEM images (middle), and histogram analysis (right) of the angle distributions for angle control. All scale bars indicate 200 nm, and all zoom-in images (images without scale bars) are 200 by 200 nm.

The cavity size of gridiron structures can be tailored by altering the number of base pairs between the adjacent junction points. An 11-by-11 gridiron structure (11 vertical helices by 11 horizontal helices) with 21 base pairs (bp) between junctions in both directions uses 5301 of 7249 nt of the M13mp18 ssDNA scaffold strand and contains 120 staple strands (42 nt each). The remaining 1948 nt of the scaffold form a single-stranded loop at one corner that is visible in atomic force microscope (AFM, FIGS. 2, A and B) and transmission electron microscope (TEM) images (FIGS. 2, C and D). Gridiron structures with 63-by-63-bp cavities (FIGS. 2, E and F) were assembled to demonstrate the programmability of the design strategy.

To test whether the ssDNA scaffold is required to force the junction to rotate and form the intended gridiron structures, we designed and successfully constructed a scaffold-free 11-by-11 gridiron structure. We also found that scaffolded and scaffold-free gridiron elements can be combined within a single structure. Further, a scaffold-free gridiron unit was examined by native gel electrophoresis to verify its formation when the component strands were mixed in equal stoichiometric ratios. Although the schematic diagram in FIG. 1D depicts 90° angles between the helices in the upper and lower layers, the angles are not fixed because the junctions are flexible. The experimental results reveal the formation of rhomboid rather than square structures; the junctions most likely behave cooperatively in order to maintain optimized base-stacking interactions and the lowest overall free energy. The single-stranded scaffold loop in one corner serves as an intrinsic marker to determine the angles adopted by the gridiron, and the angles display a bimodal distribution with nearly equal amplitudes, centered at 76° T 7° (SD) and 103° T 7°.

The flexibility of the joints makes it possible to control or reconfigure the conformation of the gridiron structure by exerting external forces on selected corners of a gridiron. A modified version of a 15-by-15 gridiron structure with 21-bp cavities has about one quadrant of the gridiron unfolded and forms a randomly coiled 836-nt single-stranded loop between two "arms" of tweezers (FIG. 2G). The ssDNA loop is long enough to allow the structure to adopt a relaxed conformation. The observed distribution of the inner angle (q) of the tweezers (measured from 309 individual structures) is broad and centered at 80° to 90°.

We could contract and extend the ssDNA loop by introducing secondary or tertiary structures that generate enough force to control the angle. Sets of staple strands were designed to either contract the ssDNA loop and fix an acute angle (a narrow distribution centered at 41° T7°) via the formation of a two-helix bundle (FIG. 2H) or to extend the loop to secure a right (FIG. 2I) or obtuse angle (FIG. 2J) via the formation of a three-helix bundle of specific length. The design with the right angle shows a narrow and symmetrical distribution centered at 94° T 10°, and the design with the obtuse angle has a broader angle distribution centered at 102° and exhibits an asymmetry that is more heavily weighted toward smaller angles.

Figure 3:
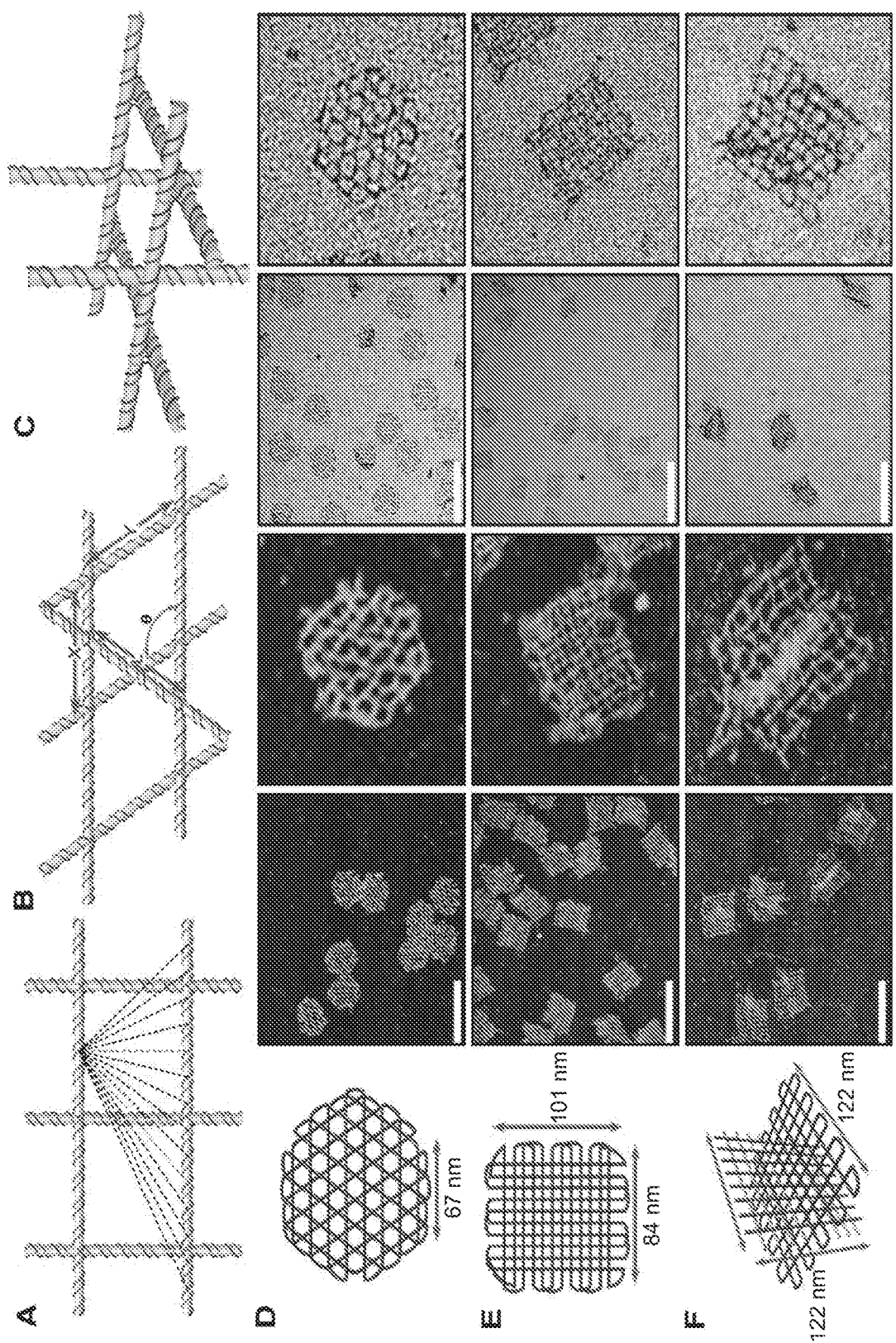
FIG. 3. Multilayer gridiron design strategies. (A and B) Strategy 1 is stacked layers. (A) A portion of a double-layer gridiron lattice with 52-bp cavity size. The yellow circles designate the permissible connection points to a third layer. The dashed lines correspond to possible connection points to form additional layers. (B) Given the double-layer gridiron lattice (X and Y lengths) and the distance between crossover points in the third layer, the angle q can be calculated as $180°-\cos-1[(X2+Y2-L2)/2XY]$. (C) Strategy 2 is intertwining gridiron planes. (D to F) Schematics (left), AFM (middle), and TEM (right) images of (D) a three-layer hexagonal gridiron design, q=120°; (E) a four-layer gridiron design, q is not controlled because the dashed green line in (A) represents a connection strategy that cannot fix the angle; and (F) a 3D gridiron assembled by using strategy 2. All scale bars indicate 200 nm, and all zoom-in images (images without scale bars) are 200 by 200 nm.
Figure 4:
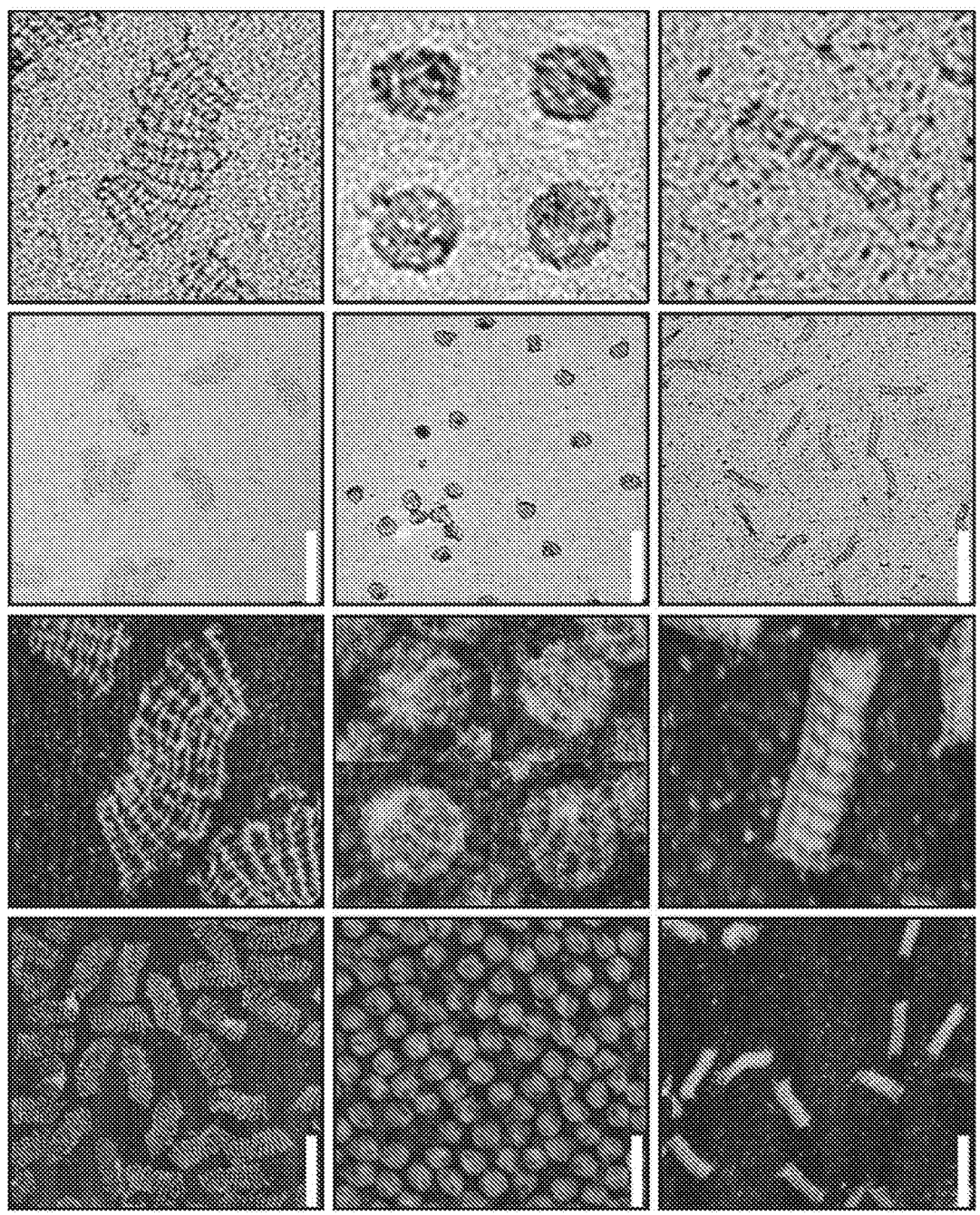
FIG. 4. Schematics (left), AFM (middle), and TEM images (right) of (A) an S-shaped structure, (B) a sphere, and (C) a screw. All scale bars indicate 200 nm, and all zoom-in images (images without scale bars) are 200 by 200 nm. In (B) and (C), the diameter and the width, respectively, appear to be larger in the AFM images compared with the TEM images. This difference is probably a result of flattening of the 3D objects into two-layer structures and AFM tip convolution.

We extended the gridiron design into the third dimension by three different strategies. The first involves stacking multiple layers of 2D gridiron lattices at selected connection points (FIGS. 3, A and B). The second relies on intertwining several gridiron planes in x-y-z directions (FIG. 3C). The third method has its basis in distorting a single layer of DNA gridiron into 3D structures by controlling their curvatures (FIG. 4). By using the first strategy, we constructed a three-layer hexagonal (FIG. 3D), a four-layer rectangular gridiron (FIG. 3E), and a three-layer parallelogram structure. For all multilayer gridiron structures, the scaffold strand raster fills each layer, with an off-set in the angle formed between the helices of adjacent layers. The three-layer hexagonal and four-layer rectangular structures maintained 60° and 90° offsets between layers, respectively.

Varying the location and distance between connection points will yield differently patterned multilayer structures. In contrast to the angle flexibility present in the quasi-2D structures, the addition of a third layer fixes the angles at junction points. The only exception to this is for connections through the center of the same unit motif, as shown by the green dashed line (FIG. 3A). In a 3D model of an eight-by-eight-by-eight three-layer hexagonal gridiron structure (FIG. 3D), neighboring junctions in the top and bottom layers are 52 bp apart, and neighboring junctions in the middle layer (alternating connections to the top and bottom layers) are 26 bp apart. Because X=Y=L (FIG. 3B), each junction should adopt a 60° torsion angle. A four-layer rectangular gridiron structure (FIG. 3E) can be broken down into two six-by-five double-layer gridirons (with 52-bp cavities) stacked on top of one another with a 26-bp offset in the connections between the first and third, and second and fourth, layers.

The relations of the lattice planes in gridiron structures are not restricted to stacked multilayer structures. The 3D gridiron structures can also be assembled by integrating gridiron lattices with scaffold-free elements. FIG. 3F presents such a design in which a nine-by-nine gridiron plane (shown in blue) is intertwined with an eight-by-eight scaffold-free gridiron plane (shown in yellow). The complex, interwoven topology of this particular structure required combining scaffolded and scaffold-free components.

Gridiron designs can allow assembly of even more complex structures by inducing a desired curvature in the basic structural unit described in nonparallel helices. The relation between adjacent linear helices (the angles formed by their theoretical intersection) between adjacent linear helices was varied. Some 3D gridiron structures that contain curvature were also achieved, such as the sphere shown in FIG. 4B. The helices in concentric ring and radial spoke layers are stretched in the center and shrunk at the edges, forming a latitudinal and longitudinal framework, respectively. This is realized by progressively adjusting the distance between junctions in latitudinal directions. Additional modifications to the basic structural motif can be used to produce other complex structures. In the screw structure (FIG. 4C), the polarity of the DNA strands in the square unit motif differs from what is illustrated in FIG. 1B (where adjacent scaffold helices have an antiparallel polarity in one direction and the same polarity in the other direction). The scaffold strand is arranged in an antiparallel configuration to form a wireframe cylinder structure (11 helices are arranged axially) and subsequently wraps around the cylinder (analogous to a left-handed screw) until the two ends meet. The distance between adjacent axial helices is 21 bp, the interthread distance is 42 bp, and the AFM and TEM images display the expected left-handed conformation.

The design principles of creating gridiron units allow scaffold strands to travel in multiple directions, which represent an important departure from certain aspects of the previous DNA origami methods. Traditional Holliday junctions do not naturally adopt conformations that would allow them to be connected in such a way, and it was unexpected to find that these motifs could (within a larger network of crossovers) endure a 150° rotation of one of the arms while simultaneously maintaining their integrity. Indeed, the flexible and dynamic behavior of these motifs may have excluded these types of junction conformations for consideration in scaffolded structures. Yield analysis from agarose gel and TEM images shows that the structures, even without purification, form with reasonably high yield (from ~36% for the gridiron tweezers to ~85% for the gridiron screw, estimated from agarose gels; from ~51% for the gridiron sphere to ~89% for the four-layer gridiron, estimated from TEM images; see supplementary materials for yield analysis). The ability to engineer DNA gridirons that are analogous to vector-based objects, where a series of points with defined positions in 3D space are connected by lines, is an important milestone in the development of synthetic nucleic acid structures. In particular, this opens up new opportunities to implement the design of complex wireframe structures that are amenable to dynamic controls. A future challenge in DNA origami is to achieve true folding, starting from a 2D sheet (miura ori), rather than the 1D M13 scaffolds commonly used in traditional DNA origami construction. The loose 2D networks and freely rotating hinges between different planes of DNA gridirons provide the design features necessary to implement Miura ori type of origami.

EXAMPLES

It should be understood that these Examples, while indicating preferred embodiments of the invention, are given by way of illustration only. From the above discussion and these following Examples, one skilled in the art can ascertain the essential characteristics of this invention, and without departing from the spirit and scope thereof, can make various changes and modifications of the invention to adapt it to various uses and conditions.

Materials and Methods

All staple strands were purchased from Integrated DNA Technologies Inc. (www.IDTDNA.com) in the format of 96-well plates at a 25 nmole synthesis scale. All the strands were normalized to 200 μM×100 μL and were used without further purification. M13mp18 single stranded DNA was purchased from New England Biolabs (NEB, Catalog number: # N4040S) and was used as received.

Assembly of 2D and 3D DNA nanostructures. The design and sequences of the DNA oligos used to form a particular structure are listed below. For each design, 10 nM of single stranded M13mp18 DNA (7,249 nucleotides) was mixed with a 10 times molar excess of staple strands in TAE Mg2+ buffer (40 mM Tris, 20 mM Acetic acid, 2 mM EDTA and 12.5 mM Magnesium acetate, pH 8.0). The resulting solutions were annealed from 95° C. to 4° C. to form the designed structures. The exact temperature steps for the slow anneal are as follows: 94 to 86° C. at 4° C. per 5 minutes; 85 to 70° C. at 1° C. per 5 minutes; 70 to 40° C. at 1° C. per 15 minutes; 40 to 25° C. at 1° C. per 10 minutes. The exact temperature steps for the fast anneal are as follows: 90 to 76° C. at 2° C. per 5 minutes; 76 to 24° C. at 4° C. per 5 minutes. All structures form in both anneal protocols. All samples are then subjected to AFM imaging and TEM imaging without further purification.

AFM imaging. For AFM imaging, the sample (2 L) was deposited onto a freshly cleaved mica surface (Ted Pella, Inc.) and left to adsorb for 2 min. 50 L buffer (1×TAE-Mg2+, plus 2 L 100 mM NiCl2) was added onto the mica, and the sample was scanned on a Veeco 8 AFM in the Scanasyst in Fluid mode using scanasyst in fluid+ tips (Veeco, Inc.).

TEM imaging: TEM samples were prepared by dropping 2 μL of the sample solution on a carbon-coated grid (400 mesh, Ted Pella). Before depositing the sample, the grids were negatively glow discharged (Emitech K100X). After 1 minute, the excess sample was wicked away from the grid with a piece of filter paper. To remove the excess salt, the grid was washed with a drop of nanopure water and the excess water was wicked away with filter paper. For staining, the grid was treated with a drop of 0.7% uranyl formate solution and the excess solution was removed with filter paper. The grid was treated with a second drop of uranyl formate solution for 20 seconds, and the excess solution was removed with filter paper. The grid was subsequently held at room temperature in air to evaporate the excess solution. TEM studies were conducted with a Philips CM12 transmission electron microscope, operated at 80 kV in bright field mode.

Agarose Gel electrophoresis: The folding products were subject to native gel electrophoresis on 0.75% agarose gel (1×TAE-Mg2+, preloaded in the gel with 0.5 μg/mL ethidium bromide) at 75-80 V for two to three hours and the gels were visualized under UV light.

Page Gel electrophoresis: The folding products were subject to native gel electrophoresis on 6% Native PAGE gel (polyacrymide; 1×TAE-Mg2+) at 200V for 2 hours at 20 degree and the gels were visualized under UV light.

Design details and sequences of assembled structures. "Tiamat" software was used to design all DNA Gridiron structures. Tiamat is a basic DNA drawing software program (similar programs also exist) and no special algorithms were used to design the DNA Gridiron structures. Most of the design tasks were performed manually and Tiamat was primarily used to generate staple strands sequences according to the scaffold strand sequence.

Figure 5:
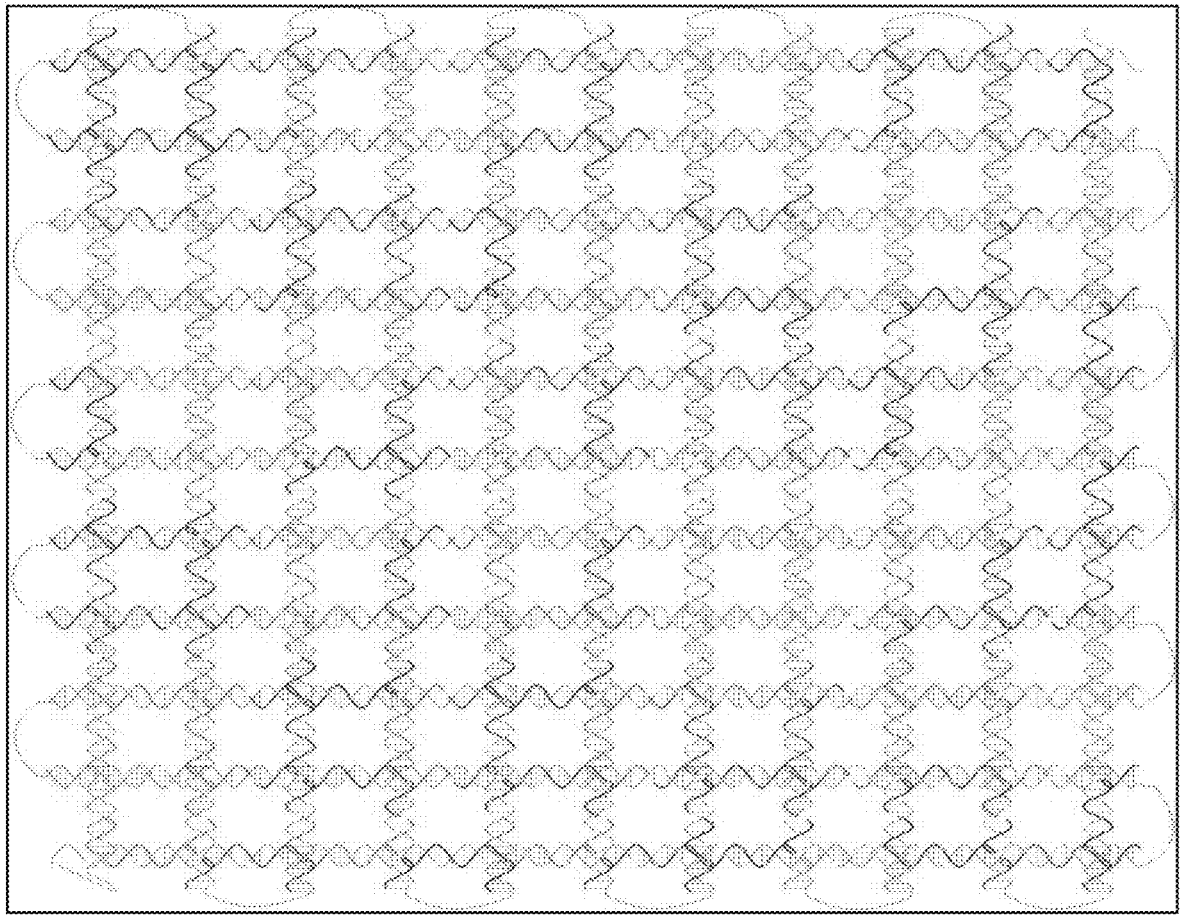
FIG. 5 shows sequences of the staples in the 21 bps Gridiron structure.

FIG. 5 illustrates the design details and staple strand sequences of some example DNA Gridiron structures. Tiamat software and files for all designs are available for downloading at the following website: skydrive.live.com/redir?resid=2416F4B1C095AF65!152& authkey=!AELrUerdPdo1P1w.

TABLE 1

Sequences of the staples in the 21 bps Gridiron structure

| Name (No.) | Sequence |
|---|---|
| 21 bpsGridiron-1 | GAAAATTCATAAGTAAGCGTCATACATGGCTTAGACGGGAGA (SEQ ID NO. 1) |
| 21 bpsGridiron-2 | ATATTCACAAAATAAAAACAGGGAAGCGCATTTTGATGATAC (SEQ ID NO. 2) |
| 21 bpsGridiron-3 | AGGAGTGTACTAATAAACAGCCATATTATTTAATTGGCCTTG (SEQ ID NO. 3) |
| 21 bpsGridiron-4 | GCCAGTTACAAGGTAATAAGTTTTAACGGGGTGTCCTGAACA (SEQ ID NO. 4) |
| 21 bpsGridiron-5 | GCAGAACGCGCGAGGTTGAGGCAGGTCAGACGTCCCAATCCA (SEQ ID NO. 5) |
| 21 bpsGridiron-6 | AATAAGAAACGGACTTGAGCCATTTGGGAATTTTCAGCTAAT (SEQ ID NO. 6) |
| 21 bpsGridiron-7 | GAGAGAATAACCAAATAAATCCTCATTAAAGCAAAAGGGCGA (SEQ ID NO. 7) |
| 21 bpsGridiron-8 | AGCATTGACAGCTGTTTATCAACAATAGATAACAGTGCCTTG (SEQ ID NO. 8) |
| 21 bpsGridiron-9 | AGTAACAGTGCCCAGTAATAAGAGAATATAAAAGCCGCCGCC (SEQ ID NO. 9) |
| 21 bpsGridiron-10 | GCATTTTCGAGCCGTATAAACAGTTAATGCCCTATCAAAATC (SEQ ID NO. 10) |
| 21 bpsGridiron-11 | ATTAAGACGCTCGCCACCAGAACCACCACCAGGTACCGACAA (SEQ ID NO. 11) |
| 21 bpsGridiron-12 | AAGGTAAAGTAAGCACCATTACCATTAGCAAGGATAGCTTAG (SEQ ID NO. 12) |
| 21 bpsGridiron-13 | TTTACCGTTCCTGGTTTACCAGCGCCAAAGACCAGAATGGAAAG (SEQ ID NO. 13) |
| 21 bpsGridiron-14 | CATTCAACCGATTGACGGAAATTATTCATTAAAGCCTTTACA (SEQ ID NO. 14) |
| 21 bpsGridiron-15 | GAAAATAGCAGGTGAATTATCACCGTCACCATTTTTTGTT (SEQ ID NO. 15) |
| 21 bpsGridiron-16 | GCAAAGACACCGTAAATGAATTTTCTGTATGGTAATTGAGCG (SEQ ID NO. 16) |
| 21 bpsGridiron-17 | TAGCATTCCACACCCTGAACAAAGTCAGAGGGGATTTTGCTA (SEQ ID NO. 17) |
| 21 bpsGridiron-18 | AACAACTTTCACGCTAACGAGCGTCTTTCCAGACAACGCCTG (SEQ ID NO. 18) |
| 21 bpsGridiron-19 | AATCTTACCAAACAGTTTCAGCGGAGTGAGAAATGTAGAAAC (SEQ ID NO. 19) |
| 21 bpsGridiron-20 | AGAAAAATAATGTTTCGTCACCAGTACAAACTAGCCTAATTT (SEQ ID NO. 20) |
| 21 bpsGridiron-21 | ATTAACTGAACAGACAGCCCTCATAGTTAGCGACAATCAATA (SEQ ID NO. 21) |
| 21 bpsGridiron-22 | AACAACATGAGAGCCAGCAAAATCACCAGTATTCTGTCCA (SEQ ID NO. 22) |
| 21 bpsGridiron-23 | CGTAACACTGAATCCCATCCTAATTTACGAGCTAGAAAGGAA (SEQ ID NO. 23) |
| 21 bpsGridiron-24 | CAACTAAAGGATTAACAACGCCAACATGTAATACCCATGTAC (SEQ ID NO. 24) |
| 21 bpsGridiron-25 | AATCGCCATATATTGCGAATAATAATTTTTTCGCTTAGGTTG (SEQ ID NO. 25) |
| 21 bpsGridiron-26 | ATAGGTCTGAGGGATAGCAAGCCCAATAGGATTAGGCAGAG (SEQ ID NO. 26) |
| 21 bpsGridiron-27 | TCCAGACGTTAACGGAATAAGTTTATTTTGTCTAACGATCTAAA (SEQ ID NO. 27) |
| 21 bpsGridiron-28 | TCGCCCACGCAGCCATTGCAACAGGAAAAATGCGCCGACA (SEQ ID NO. 28) |
| 21 bpsGridiron-29 | CCTCATTTTCAAGACTACCTTTTTAACCTCCGACGTTGAAAA (SEQ ID NO. 29) |
| 21 bpsGridiron-30 | TCTCCAAAAAATGAATTACCTTTTTAATGGAGAGCCACCAC (SEQ ID NO. 30) |
| 21 bpsGridiron-31 | ATATAAGTATTTGACGCTCAATCGTCTGAAGATAAGTGCC (SEQ ID NO. 31) |
| 21 bpsGridiron-32 | ACCCTCAGAGCGAGAAGAGTCAATAGTGAATTCCTGCCTATT (SEQ ID NO. 32) |
| 21 bpsGridiron-33 | TCGGAACCTATTGTGAGTGAATAACCTTGCTTCAGAGCCACC (SEQ ID NO. 33) |
| 21 bpsGridiron-34 | CGTTTGCCAATTCACCAGTCACACGACCAGTTCGGTCATA (SEQ ID NO. 34) |
| 21 bpsGridiron-35 | AAACATAGCGCCGGAAACGTCACCAATGAATAATTTTCCC (SEQ ID NO. 35) |

TABLE 1-continued

Sequences of the staples in the 21 bps Gridiron structure

| Name (No.) | Sequence |
|---|---|
| 21 bpsGridiron-36 | ACAATTTCATTAAGGCTCCAAAAGGAGCCTTTTATACTTCTG (SEQ ID NO. 36) |
| 21 bpsGridiron-37 | GAACAAAGAATCAGTAGCGACAGAATCAAGTTGAGTAACA (SEQ ID NO. 37) |
| 21 bpsGridiron-38 | GATAATACATTTGCTTTCGAGGTGAATTTCTTAGCCCTAAAA (SEQ ID NO. 38) |
| 21 bpsGridiron-39 | ACAGAGATATAGCGCGTTTTCATCGGCATTTAATAAAAGG (SEQ ID NO. 39) |
| 21 bpsGridiron-40 | ATTTTAAAAGTTTTGCCTTTAGCGTCAGACTGGAACCCTTCT (SEQ ID NO. 40) |
| 21 bpsGricaron-41 | GACCTGAAAGCCGGAACCAGAGCCACCACCGGAACGTTATTA (SEQ ID NO. 41) |
| 21 bpsGridiron-42 | ATCAAAATCACGTAAGAATACGTGGCACAGACGGTTTTGCTC (SEQ ID NO. 42) |
| 21 bpsGridiron-43 | AGTACCAGGCGATGGATTATTTACATTGGCAGTCTTTTCATA (SEQ ID NO. 43) |
| 21 bpsGricaron-44 | AATTCGACAACGAGAAGGATTAGGATTAGCGGAATATTTTTG (SEQ ID NO. 44) |
| 21 bpsGridiron-45 | AATGGCTATTACCGTACTCAGGAGGTTTAGTACTTTACAAAC (SEQ ID NO. 45) |
| 21 bpsGridiron-46 | TAGGTGTATCAGTCTTTAATGCGCGAACTGATAAACAGCTTG (SEQ ID NO. 46) |
| 21 bpsGricaron-47 | ATACCGATAGTCGCTCATGGAAATACCTACATTAGCCCGGAA (SEQ ID NO. 47) |
| 21 bpsGridiron-48 | GTTTATCAGCTTGAGGATTTAGAAGTATTAGACCGCCACCCT (SEQ ID NO. 48) |
| 21 bpsGridiron-49 | CAGAACCGCCATATAATCCTGATTGTTTGGATAATTGTATCG (SEQ ID NO. 49) |
| 21 bpsGricaron-50 | AGACTCCTCAATCGTATTAAATCCTTTGCCCGAACCGCCTCC (SEQ ID NO. 50) |
| 21 bpsGridiron-51 | CTCAGAGCCGCTATCATCATATTCCTGATTATTAAGAGGCTG (SEQ ID NO. 51) |
| 21 bpsGridiron-52 | TCGCTATTAATACCATCGATAGCAGCACCGTAAACCACCAGA (SEQ ID NO. 52) |
| 21 bpsGricaron-53 | AGGAGCGGAATCACCCTCAGAACCGCCACCCTCTGTAAATCG (SEQ ID NO. 53) |
| 21 bpsGridiron-54 | AAATCAATATATATTCTGAAACATGAAAGTATCAGATGATGG (SEQ ID NO. 54) |
| 21 bpsGridiron-55 | CAATTCATCAACCCTCAGAACCGCCACCCTCAAACAGTACAT (SEQ ID NO. 55) |
| 21 bpsGricaron-56 | GGTTATATAACCGGCTACAGAGGCTTTGAGGACTTAATTGAG (SEQ ID NO. 56) |
| 21 bpsGridiron-57 | TAAGGCGTTCCCAATTCTGCGAACGAGTAGTGAAATACCG (SEQ ID NO. 57) |
| 21 bpsGridiron-58 | GCTTAATTGCTAACGCAATAATAACGGAATACAGGTCATTTTG (SEQ ID NO. 58) |
| 21 bpsGridiron-59 | TAATTTCATCTACTTCAAATATCGCGTTTTAATCATAATTAC (SEQ ID NO. 59) |
| 21 bpsGridiron-60 | TAGAAAAAGCCGTTTACCAGACGACGATAAAAATATTTTAGT (SEQ ID NO. 60) |
| 21 bpsGridiron-61 | AGTTGAGATTTAGACTCCTTATTACGCAGTATATTATTACAGGT (SEQ ID NO. 61) |
| 21 bpsGridiron-62 | AAGACAAAGAATAATCATTGTGAATTACCTTATACAAATTCT (SEQ ID NO. 62) |
| 21 bpsGridiron-63 | TACCAGTATAATCCATGTTACTTAGCCGGAACATCCAATCGC (SEQ ID NO. 63) |
| 21 bpsGridiron-64 | ATCTTTGACCCATACATAAAGGTGGCAACATAGGCAAAAGAATA (SEQ ID NO. 64) |
| 21 bpsGridiron-65 | AACCGAGGAGAATATAATGCTGTAGCTCAAGCCGAACAAA (SEQ ID NO. 65) |
| 21 bpsGridiron-66 | CTAATATCAGAGCACCAACCTAAAACGAAAGATAAAAGAAAC (SEQ ID NO. 66) |
| 21 bpsGridiron-67 | CCACTACGAAGGAGATAACCCACAAGAATTGAAAACAAAGTA (SEQ ID NO. 67) |
| 21 bpsGridiron-68 | CAACGGAGATTCTATTTTGCACCCAGCTACAAATACGTAATG (SEQ ID NO. 68) |
| 21 bpsGridiron-69 | TAGAAGGCTAAGTACGGTGTCTGGAAGTTTCCCAATAGCA (SEQ ID NO. 69) |
| 21 bpsGridiron-70 | CAATCAATAATAGTTTCCATTAAACGGGTAAATTTTATCCTG (SEQ ID NO. 70) |
| 21 bpsGridiron-71 | TTTCATGAGGACGGCTGTCTTTCCTTATCATTGTGTCGAAAT (SEQ ID NO. 71) |
| 21 bpsGridiron-72 | CCGCGACCTGCAGCCAACGCTCAACAGTAGGGCTAAAGACTT (SEQ ID NO. 72) |
| 21 bpsGridiron-73 | AAGATTAGTTGTGTATCATCGCCTGATAAATTCCAAGAACGG (SEQ ID NO. 73) |

TABLE 1-continued

Sequences of the staples in the 21 bps Gridiron structure

| Name (No.) | Sequence |
|---|---|
| 21 bpsGridiron-74 | GTATTAAACCAATTATACCAGTCAGGACGTTGGCCTTAAATC (SEQ ID NO. 74) |
| 21 bpsGridiron-75 | AGAACTGGCTCAGTACCGCACTCATCGAGAACAGCAACACTA (SEQ ID NO. 75) |
| 21 bpsGridiron-76 | TCATAACCCTCTGTTTAGTATCATATGCGTTATGCGATTTTA (SEQ ID NO. 76) |
| 21 bpsGridiron-77 | AGCGAACCTCCGGAATTACGAGGCATAGTAAGAAGCAAGCCG (SEQ ID NO. 77) |
| 21 bpsGridiron-78 | TTTTTATTTTCGACCGGAAGCAAACTCCAACAGAGGCGTTTT (SEQ ID NO. 78) |
| 21 bpsGridiron-79 | AAAGCGAACCAATCGTAGGAATCATTACCGCGCATTCCATAT (SEQ ID NO. 79) |
| 21 bpsGridiron-80 | AACAGTTGATTAAATAAGAATAAACACCGGAATTCGAGCTTC (SEQ ID NO. 80) |
| 21 bpsGridiron-81 | ATATGCAACTATATCCGGTATTCTAAGAACGCGGTCAGGATT (SEQ ID NO. 81) |
| 21 bpsGridiron-82 | AGAGAGTACCTTTTAAGAAAAGTAAGCAGATACATGTTTTAA (SEQ ID NO. 82) |
| 21 bpsGricaron-83 | TAACGCCAAAACGACTTGCGGGAGGTTTTGAAGGAAGAAAAA (SEQ ID NO. 83) |
| 21 bpsGridiron-84 | TCTACGTTAATAAGAAACAATGAAATAGCAATTGCAGATACA (SEQ ID NO. 84) |
| 21 bpsGridiron-85 | GTAGAAAATACCCAGCGATTATACCAAGCGCGGTTAAGCCCA (SEQ ID NO. 85) |
| 21 bpsGricaron-86 | ATAATAAGAGCAAAACGAACTAACGGAACAACGTTAGCAAAC (SEQ ID NO. 86) |
| 21 bpsGridiron-87 | TGGCATGATTAAGGAATACCACATTCAACTAAAGCTATCTTA (SEQ ID NO. 87) |
| 21 bpsGridiron-88 | CCGAAGCCCTTTTAATTGCTCCTTTTGATAAGCCAAAAGAAC (SEQ ID NO. 88) |
| 21 bpsGridiron-89 | AAGCCCGAAAGTCTGACCTAAATTTAATGGTTATTTAGTTTG (SEQ ID NO. 89) |
| 21 bpsGridiron-90 | ACCATTAGATAGATTGCTTTGAATACCAAGTTGATTAAGAGG (SEQ ID NO. 90) |
| 21 bpsGridiron-91 | TAAACAGTTTTGATTAGTAATAACATCACCATTGAATCC (SEQ ID NO. 91) |
| 21 bpsGricaron-92 | AATTTCAACTTCGCGAGAAAACTTTTTCAAATACCAAAATAG (SEQ ID NO. 92) |
| 21 bpsGridiron-93 | CGAGAGGCTTTTTATTCATTTCAATTACCTGAGAGATGGTTT (SEQ ID NO. 93) |
| 21 bpsGridiron-94 | ATTCATTACAACTATCGGCCTTGCTGGTAAAGTAATCTTG (SEQ ID NO. 94) |
| 21 bpsGricaron-95 | GAGGGTAGCAATATATGTAAATGCTGATGCAAGAGGCGCAGA (SEQ ID NO. 95) |
| 21 bpsGridiron-96 | CGGTCAATCATAACATCAAGAAAACAAAATTAGCATCGGAAC (SEQ ID NO. 96) |
| 21 bpsGridiron-97 | GATTCGCCTCATTTCGCAAATGGTCAATAATTACATCGGG (SEQ ID NO. 97) |
| 21 bpsGricaron-98 | AATAATGGAAGCACCCTCAGCAGCGAAAGACAATTACATTTA (SEQ ID NO. 98) |
| 21 bpsGridiron-99 | TGCGGGATCGTGGTTAGAACCTACCATATCAATTTGAAAGAG (SEQ ID NO. 99) |
| 21 bpsGridiron-100 | GACAGATGAACACTAACAACTAATAGATTAGAAGGCCGCTTT (SEQ ID NO. 100) |
| 21 bpsGridiron-101 | CTCAAATATTTGGGGCGCGAGCTGAAAAGGTCTAAAGCAT (SEQ ID NO. 101) |
| 21 bpsGridiron-102 | CATCGCCATTACTGAGGCTTGCAGGGAGTTAAGCCGTCAATA (SEQ ID NO. 102) |
| 21 bpsGridiron-103 | ATATTCGGTCGAAAATACCGAACGAACCACCAGGCTGGCTGA (SEQ ID NO. 103) |
| 21 bpsGridiron-104 | CCTTCATCAAGTATCCAGAACAATATTACCGCCATAACCGAT (SEQ ID NO. 104) |
| 21 bpsGridiron-105 | TCTTTAGGAGCGGTGTACAGACCAGGCGCATAGCAGAAGATA (SEQ ID NO. 105) |
| 21 bpsGridiron-106 | AAACAGAGGTGGCTCATTCAGTGAATAAGGCTATCTAAAATA (SEQ ID NO. 106) |
| 21 bpsGridiron-107 | GTAACAAAGCTAGGCGGTCAGTATTAACACCGTGCGGAATCG (SEQ ID NO. 107) |
| 21 bpsGridiron-108 | TCATAAATATTTTGCCTGAGTAGAAGAACTCACCAAATCAAC (SEQ ID NO. 108) |
| 21 bpsGridiron-109 | AAATCAACAGTAGACTGGATAGCGTCCAATACCCTGCAACAG (SEQ ID NO. 109) |
| 21 bpsGridiron-110 | TGCCACGCTGAAATCAAAAATCAGGTCTTTACGTCAGTTGGC (SEQ ID NO. 110) |
| 21 bpsGridiron-111 | GAATGACCATAGAGCCAGCAGCAAATGAAAAATGGCATCAAT (SEQ ID NO. 111) |

TABLE 1-continued

Sequences of the staples in the 21 bps Gridiron structure

| Name (No.) | Sequence |
|---|---|
| 21 bpsGridiron-112 | TCTACTAATAGTAACCGTTGTAGCAATACTTCCAGAAAACGA (SEQ ID NO. 112) |
| 21 bpsGridiron-113 | TATATTTTCATCAAACCCTCAATCAATATCTGCCTGACTATT (SEQ ID NO. 113) |
| 21 bpsGridiron-114 | ATAGTCAGAAGAATATACAGTAACAGTACCTTCCTGTTTAGC (SEQ ID NO. 114) |
| 21 bpsGridiron-115 | GTAAAATGTTTTGAAAGGAATTGAGGAAGGTTTGCCCTGACG (SEQ ID NO. 115) |
| 21 bpsGridiron-116 | AGAAACACCAGAAATAAAGAAATTGCGTAGATGGGGTAATA (SEQ ID NO. 116) |
| 21 bpsGridiron-117 | ATGATGAAACAAAGGGAACCGAACTGACCAACAATTATTTGC (SEQ ID NO. 117) |
| 21 bpsGridiron-118 | ACGTAAAACAGAACGAGTAGTAAATTGGGCTTGCAAAAGAAG (SEQ ID NO. 118) |
| 21 bpsGridiron-119 | GCAGAGGCGAATGCAAAAGAAGTTTTGCCAGATTTCAGGTTT (SEQ ID NO. 119) |
| 21 bpsGridiron-120 | AACGTCAGATGCAAAGCGGATTGCATCAAAAAACAAATCGC (SEQ ID NO. 120) |

TABLE 2

Sequences of the staples in the 42 bps Gridiron structure

| Name (No.) | Sequence |
|---|---|
| 42 bpsGridiron-1 | CCTCCCGACTTGCGGGAGGTTCTGCATTAATGAATCGGCCAA (SEQ ID NO. 121) |
| 42 bpsGridiron-2 | TAACTCACATTAATTGCGTTGAGAATTAACTGAACACCCTGA (SEQ ID NO. 122) |
| 42 bpsGridiron-3 | AAAATGAAAATAGCAGCCTTTTTAAATTTTTGTTAAATCAGC (SEQ ID NO. 123) |
| 42 bpsGridiron-4 | AACAGGAAGATTGTATAAGCATACAATTTTATCCTGAATCTT (SEQ ID NO. 124) |
| 42 bpsGridiron-5 | AGTTGCTATTTTGCACCCAGCAATATTTAAATTGTAAACGTT (SEQ ID NO. 125) |
| 42 bpsGridiron-6 | AATATTTTGTTAAAATTCGCAACAGAGAGAATAACATAAAAA (SEQ ID NO. 126) |
| 42 bpsGridiron-7 | CAGGGAAGCGCATTAGACGGGCGCTCACTGCCCGCTTTCCAG (SEQ ID NO. 127) |
| 42 bpsGridiron-8 | TCGGGAAACCTGTCGTGCCAGTTGAAGCCTTAAATCAAGATT (SEQ ID NO. 128) |
| 42 bpsGridiron-9 | ACCAACGCTAACGAGCGTCTTTGTCAATCATATGTACCCCGG (SEQ ID NO. 129) |
| 42 bpsGridiron-10 | GGTCATTGCCTGAGAGTCTGGACGATTTTTGTTTAACGTCA (SEQ ID NO. 130) |
| 42 bpsGridiron-11 | TTATCCCAATCCAAATAAGAAAGCAAACAAGAGAATCGATGA (SEQ ID NO. 131) |
| 42 bpsGridiron-12 | ACGGTAATCGTAAAACTAGCATCCAGAGCCTAATTTGCCAGT (SEQ ID NO. 132) |
| 42 bpsGridiron-13 | CCGCCACCCTCAGAGCCACCATTTCATCAACATTAAATGTGA (SEQ ID NO. 133) |
| 42 bpsGridiron-14 | TCATTTTTTAACCAATAGGAAGTAGCGCGTTTTCATCGGCAT (SEQ ID NO. 134) |
| 42 bpsGridiron-15 | AACCATCGATAGCAGCACCGTTGGGGTGCCTAATGAGTGAGC (SEQ ID NO. 135) |
| 42 bpsGridiron-16 | AGCTTGCATGCCTGCAGGTCGTAGTTGCGCCGACAATGACAA (SEQ ID NO. 136) |
| 42 bpsGridiron-17 | TTTCGGTCATAGCCCCCTTATAGAGATCTACAAAGGCTATCA (SEQ ID NO. 137) |
| 42 bpsGridiron-18 | CCTCATATATTTTAAATGCAAAAAAAAGGCTCCAAAAGGAGC (SEQ ID NO. 138) |
| 42 bpsGridiron-19 | TTTCACGTTGAAAATCTCCAATGCCTGAGTAATGTGTAGGTA (SEQ ID NO. 139) |
| 42 bpsGridiron-20 | AAGATTCAAAAGGGTGAGAAATGAGAATAGAAAGGAACAACT (SEQ ID NO. 140) |
| 42 bpsGridiron-21 | TCATAGTTAGCGTAACGATCTTGGTCATAGCTGTTTCCTGTG (SEQ ID NO. 141) |
| 42 bpsGridiron-22 | CCGAGCTCGAATTCGTAATCAAAAGTTTTGTCGTCTTTCCAG (SEQ ID NO. 142) |
| 42 bpsGridiron-23 | ACGTTAGTAAATGAATTTCTTCTCCGTGGGAACAAACGGCG (SEQ ID NO. 143) |
| 42 bpsGridiron-24 | GCGAGTAACAACCCGTCGGATGTATGGGATTTTGCTAAACAA (SEQ ID NO. 144) |
| 42 bpsGridiron-25 | CTTTAATTGTATCGGTTTATCTCACGTTGGTGTAGATGGGCG (SEQ ID NO. 145) |

TABLE 2-continued

Sequences of the staples in the 42 bps Gridiron structure

| Name (No.) | Sequence |
|---|---|
| 42 bpsGridiron-26 | GATTGACCGTAATGGGATAGGAGCTTGCTTTCGAGGTGAATT (SEQ ID NO. 146) |
| 42 bpsGridiron-27 | CTTTCAACAGTTTCAGCGGAGGGCCGGAGACAGTCAAATCAC (SEQ ID NO. 147) |
| 42 bpsGridiron-28 | CATCAATATGATATTCAACCGTCAGAGCCGCCACCCTCAGAA (SEQ ID NO. 148) |
| 42 bpsGridiron-29 | CCACCACCGGAACCGCCTCCCTTCTAGCTGATAAATTAATGC (SEQ ID NO. 149) |
| 42 bpsGridiron-30 | TGAAATTGTTATCCGCTCACAGCATTGACAGGAGGTTGAGGC (SEQ ID NO. 150) |
| 42 bpsGridiron-31 | CCACCACCAGAGCCGCCGCCAATTCCACACAACATACGAGCC (SEQ ID NO. 151) |
| 42 bpsGridiron-32 | TCTGGCCTTCCTGTAGCCAGCCCCTCAGAGCCGCCACCAGAA (SEQ ID NO. 152) |
| 42 bpsGridiron-33 | CGGAGAGGGTAGCTATTTTTGTAGCGTTTGCCATCTTTTCAT (SEQ ID NO. 153) |
| 42 bpsGridiron-34 | TCTTAAACAGCTTGATACCGAACTCTAGAGGATCCCCGGGTA (SEQ ID NO. 154) |
| 42 bpsGridiron-35 | GGAAGCATAAAGTGTAAAGCCAATCAGTAGCGACAGAATCAA (SEQ ID NO. 155) |
| 42 bpsGridiron-36 | GTTTGCCTTTAGCGTCAGACTCGCCATCAAAAATAATTCGCG (SEQ ID NO. 156) |
| 42 bpsGridiron-37 | ACAGGTAGAAAGATTCATCAGACTCCAGCCAGCTTTCCGGCA (SEQ ID NO. 157) |
| 42 bpsGridiron-38 | CATCGTAACCGTGCATCTGCCTGGTTTAATTTCAACTTTAAT (SEQ ID NO. 158) |
| 42 bpsGridiron-39 | ATTCAGTGAATAAGGCTTGCCGTAAAACGACGGCCAGTGCCA (SEQ ID NO. 159) |
| 42 bpsGridiron-40 | CATTGTGAATTACCTTATGCGAAGGATAAAAATTTTTAGAAC (SEQ ID NO. 160) |
| 42 bpsGridiron-41 | TAGCAAAATTAAGCAATAAAGTCTACTAATAGTAGTAGCATT (SEQ ID NO. 161) |
| 42 bpsGridiron-42 | CGAACGAGTAGATTTAGTTTGCGCTATTACGCCAGCTGGCGA (SEQ ID NO. 162) |
| 42 bpsGridiron-43 | GGCGATCGGTGCGGGCCTCTTACCATTAGATACATTTCGCAA (SEQ ID NO. 163) |
| 42 bpsGricaron-44 | ATGGTCAATAACCTGTTTAGCAGGCAAAGCGCCATTCGCCAT (SEQ ID NO. 164) |
| 42 bpsGridiron-45 | CCGCTTCTGGTGCCGGAAACCTATATTTTCATTTGGGGCGCG (SEQ ID NO. 165) |
| 42 bpsGridiron-46 | AGCTGAAAAGGTGGCATCAATCCTCAGAGCATAAAGCTAAAT (SEQ ID NO. 166) |
| 42 bpsGricaron-47 | CGGTTGTACCAAAAACATTATAACTAACGGAACAACATTATT (SEQ ID NO. 167) |
| 42 bpsGridiron-48 | AAAATCTACGTTAATAAAACGGACCCTGTAATACTTTTGCGG (SEQ ID NO. 168) |
| 42 bpsGridiron-49 | AAGGGGATGTGCTGCAAGGCACGCCAAAAGGAATTACGAGG (SEQ ID NO. 169) |
| 42 bpsGricaron-50 | TTCAACTAATGCAGATACATAGATTAAGTTGGGTAACGCCAG (SEQ ID NO. 170) |
| 42 bpsGridiron-51 | TATCGGCCTCAGGAAGATCGCTTGAGATTTAGGAATACCACA (SEQ ID NO. 171) |
| 42 bpsGridiron-52 | GAGAAGCCTTTATTTCAACGCATTTTAAGAACTGGCTCATTA (SEQ ID NO. 172) |
| 42 bpsGricaron-53 | GGTTTTCCCAGTCACGACGTTCTGACGAGAAACACCAGAACG (SEQ ID NO. 173) |
| 42 bpsGridiron-54 | AGTAGTAAATTGGGCTTGAGAAGTTTGAGGGGACGACGACAG (SEQ ID NO. 174) |
| 42 bpsGridiron-55 | TCTTTCCTTATCATTCCAAGACGTAAAACAGAAATAAAGAAA (SEQ ID NO. 175) |
| 42 bpsGricaron-56 | TTGTTTGGATTATACTTCTGAAAAGTTACCAGAAGGAAACCG (SEQ ID NO. 176) |
| 42 bpsGridiron-57 | AATGAAATAGCAATAGCTATCAATGGATTATTTACATTGGCA (SEQ ID NO. 177) |
| 42 bpsGridiron-58 | CCAGCCATTGCAACAGGAAAGCCGTTTTTATTTTCATCGTA (SEQ ID NO. 178) |
| 42 bpsGricaron-59 | GCACTCATCGAGAACAAGCAAACGCTCATGGAAATACCTACA (SEQ ID NO. 179) |
| 42 bpsGridiron-60 | TTTTGACGCTCAATCGTCTGATTACCGAAGCCCTTTTTAAGA (SEQ ID NO. 180) |
| 42 bpsGridiron-61 | AAAGTAAGCAGATAGCCGAACATAATGGAAGGGTTAGAACCT (SEQ ID NO. 181) |
| 42 bpsGridiron-62 | ACCATATCAAAATTATTTGCAACGGGTATTAAACCAAGTACC (SEQ ID NO. 182) |
| 42 bpsGridiron-63 | GGAATCATTACCGCGCCCAATTCAAACTATCGGCCTTGCTGG (SEQ ID NO. 183) |

TABLE 2-continued

Sequences of the staples in the 42 bps Gridiron structure

| Name (No.) | Sequence |
|---|---|
| 42 bpsGridiron-64 | AATTAACCGTTGTAGCAATACCCAATAATAAGAGCAAGAAAC (SEQ ID NO. 184) |
| 42 bpsGridiron-65 | ACAAAGTCAGAGGGTAATTGACCGCCTGGCCCTGAGAGAGTT (SEQ ID NO. 185) |
| 42 bpsGridiron-66 | TATTGGGCGCCAGGGTGGTTTAACGCGAGGCGTTTTAGCGAA (SEQ ID NO. 186) |
| 42 bpsGridiron-67 | AGGCTTATCCGGTATTCTAAGTTCTTTTCACCAGTGAGACGG (SEQ ID NO. 187) |
| 42 bpsGridiron-68 | GCAACAGCTGATTGCCCTTCAGCGCTAATATCAGAGAGATAA (SEQ ID NO. 188) |
| 42 bpsGridiron-69 | CCCACAAGAATTGAGTTAAGCTTCTTTGATTAGTAATAACAT (SEQ ID NO. 189) |
| 42 bpsGridiron-70 | CACTTGCCTGAGTAGAAGAACAGCAAGCAAATCAGATATAGA (SEQ ID NO. 190) |
| 42 bpsGridiron-71 | TTCCAGTAAGCGTCATACATGTGACCTGAAAGCGTAAGAATA (SEQ ID NO. 191) |
| 42 bpsGridiron-72 | GATTCACCAGTCACACGACCAAAGGTGAATTATCACCGTCAC (SEQ ID NO. 192) |
| 42 bpsGridiron-73 | CAAAAGGGCGACATTCAACCGAATTCATCAATATAATCCTGA (SEQ ID NO. 193) |
| 42 bpsGridiron-74 | TTTACAAACAATTCGACAACTACTTTTTCATGAGGAAGTTTC (SEQ ID NO. 194) |
| 42 bpsGridiron-75 | CAACCATCGCCCACGCATAACAAAGAACGTGGACTCCAACGT (SEQ ID NO. 195) |
| 42 bpsGridiron-76 | GCAGCAAGCGGTCCACGCTGGGGCCGGAAACGTCACCAATGA (SEQ ID NO. 196) |
| 42 bpsGridiron-77 | CGACTTGAGCCATTTGGGAATAAAGAGTCTGTCCATCACGCA (SEQ ID NO. 197) |
| 42 bpsGridiron-78 | TGGTTGCTTTGACGAGCACGTCTTTTGCGGGATCGTCACCCT (SEQ ID NO. 198) |
| 42 bpsGridiron-79 | CTTGCAGGGAGTTAAAGGCCGATAACGTGCTTTCCTCGTTAG (SEQ ID NO. 199) |
| 42 bpsGridiron-80 | AATCAGAGCGGGAGCTAAACACCGTAACACTGAGTTTCGTCA (SEQ ID NO. 200) |
| 42 bpsGridiron-81 | GGAGGTTTAGTACCGCCACCCTGAGTAACATTATCATTTTGC (SEQ ID NO. 201) |
| 42 bpsGridiron-82 | ACGTTATTAATTTTAAAAGTTTCAGAACCGCCACCCTCAGAA (SEQ ID NO. 202) |
| 42 bpsGridiron-83 | CCGCCACCCTCAGAGCCACCAGAATGGCTATTAGTCTTTAAT (SEQ ID NO. 203) |
| 42 bpsGridiron-84 | CGTGGCACAGACAATATTTTTCCCTCATTTTCAGGGATAGCA (SEQ ID NO. 204) |
| 42 bpsGridiron-85 | CAGCAGCGAAAGACAGCATCGACATCGCCATTAAAAATACCG (SEQ ID NO. 205) |
| 42 bpsGricaron-86 | GCGCGAACTGATAGCCCTAAAGAACGAGGGTAGCAACGGCTA (SEQ ID NO. 206) |
| 42 bpsGridiron-87 | AGCCCAATAGGAACCCATGTAGGAGGCCGATTAAAGGGATTT (SEQ ID NO. 207) |
| 42 bpsGridiron-88 | ATCAAAAGAATAGCCCGAGATGTAGCATTCCACAGACAGCCC (SEQ ID NO. 208) |
| 42 bpsGricaron-89 | CCAGTACAAACTACAACGCCTAGGGTTGAGTGTTGTTCCAGT (SEQ ID NO. 209) |
| 42 bpsGridiron-90 | TAGACAGGAACGGTACGCCAGGCGCAGTCTCTGAATTTACCG (SEQ ID NO. 210) |
| 42 bpsGridiron-91 | AGGTCAGACGATTGGCCTTGAAATCGGCAAAATCCCTTATAA (SEQ ID NO. 211) |
| 42 bpsGricaron-92 | CCTGTTTGATGGTGGTTCCGATATTCACAAACAAATAAATCC (SEQ ID NO. 212) |
| 42 bpsGridiron-93 | TCATTAAAGCCAGAATGGAAAAATCCTGAGAAGTGTTTTTAT (SEQ ID NO. 213) |
| 42 bpsGridiron-94 | GGAACAAAGAAACCACCAGAAGGGTCAGTGCCTTGAGTAACA (SEQ ID NO. 214) |
| 42 bpsGricaron-95 | TACTGGTAATAAGTTTTAACGGGAGCGGAATTATCATCATAT (SEQ ID NO. 215) |
| 42 bpsGridiron-96 | CCAACAGAGATAGAACCCTTCGCTTTTGATGATACAGGAGTG (SEQ ID NO. 216) |
| 42 bpsGridiron-97 | AATCAGTGAGGCCACCGAGTATAGAGCCAGCAAAATCACCAG (SEQ ID NO. 217) |
| 42 bpsGricaron-98 | TAGCACCATTACCATTAGCAATTTGCCCCAGCAGGCGAAAAT (SEQ ID NO. 218) |
| 42 bpsGridiron-99 | TTGGAACAAGAGTCCACTATTCGATATATTCGGTCGCTGAGG (SEQ ID NO. 219) |
| 42 bpsGridiron-100 | CAGAGGCTTTGAGGACTAAAGCGTATTAAATCCTTTGCCCGA (SEQ ID NO. 220) |
| 42 bpsGricaron-101 | TCCTGATTATCAGATGATGGCATTGAGGGAGGGAAGGTAAAT (SEQ ID NO. 221) |

TABLE 2-continued

Sequences of the staples in the 42 bps Gridiron structure

| Name (No.) | Sequence |
|---|---|
| 42 bpsGridiron-102 | ATTGACGGAAATTATTCATTAGTAATAAAAGGGACATTCTGG (SEQ ID NO. 222) |
| 42 bpsGridiron-103 | TTTGCCAGAGGGGTAATAGTGTGCCACGCTGAGAGCCAGCA (SEQ ID NO. 223) |
| 42 bpsGridiron-104 | AACGAACCACCAGCAGAAGATATGAACGGTGTACAGACCAGG (SEQ ID NO. 224) |
| 42 bpsGridiron-105 | CGGAACGAGGCGCAGACGGTCGAGGATTTAGAAGTATTAGAC (SEQ ID NO. 225) |
| 42 bpsGridiron-106 | CAAAGGGCGAAAAACCGTCTAATCAACGTAACAAAGCTGCTC (SEQ ID NO. 226) |
| 42 bpsGridiron-107 | CGCATAGGCTGGCTGACCTTCGCCGCTACAGGGCGCGTACTA (SEQ ID NO. 227) |
| 42 bpsGridiron-108 | CGTGGCGAGAAAGGAAGGGAAATATGCAACTAAAGTACGGTG (SEQ ID NO. 228) |
| 42 bpsGridiron-109 | AGGATTAGAGAGTACCTTTAAGAAAGGAATTGAGGAAGGTTA (SEQ ID NO. 229) |
| 42 bpsGridiron-110 | TCAGTTGGCAAATCAACAGTTTTGCTCCTTTTGATAAGAGGT (SEQ ID NO. 230) |
| 42 bpsGridiron-111 | CATTTTTGCGGATGGCTTAGATCACCTTGCTGAACCTCAAAT (SEQ ID NO. 231) |
| 42 bpsGridiron-112 | GCAAATGAAAAATCTAAAGCAGCTTAATTGCTGAATATAATG (SEQ ID NO. 232) |
| 42 bpsGridiron-113 | CTGTAGCTCAACATGTTTTAAGAAAGCGAAAGGAGCGGGCGC (SEQ ID NO. 233) |
| 42 bpsGridiron-114 | TAAAGCACTAAATCGGAACCCAACAGTTGATTCCCAATTCTG (SEQ ID NO. 234) |
| 42 bpsGridiron-115 | TCTGGAAGTTTCATTCCATATTAAAGGGAGCCCCCGATTTAG (SEQ ID NO. 235) |
| 42 bpsGridiron-116 | TAGGGCGCTGGCAAGTGTAGCAGAGGCTTTTGCAAAAGAAGT (SEQ ID NO. 236) |
| 42 bpsGridiron-117 | CATAGTAAGAGCAACACTATCTTTTTTGGGGTCGAGGTGCCG (SEQ ID NO. 237) |
| 42 bpsGridiron-118 | TGAACCATCACCCAAATCAAGATAACCCTCGTTTACCAGACG (SEQ ID NO. 238) |
| 42 bpsGridiron-119 | ACGATAAAAACCAAAATAGCGGGTCACGCTGCGCGTAACCAC (SEQ ID NO. 239) |
| 42 bpsGridiron-120 | TCTAAAATATCTTTAGGAGCAATAAATATTCATTGAATCCCC (SEQ ID NO. 240) |
| 42 bpsGridiron-121 | GTCCAATACTGCGGAATCGTCCTAACAACTAATAGATTAGAG (SEQ ID NO. 241) |
| 42 bpsGridiron-122 | GTATTAACACCGCCTGCAACAAAAATGTTTAGACTGGATAGC (SEQ ID NO. 242) |
| 42 bpsGridiron-123 | CACACCCGCCGCGCTTAATGCATCAAGAGTAATCTTGACAAG (SEQ ID NO. 243) |
| 42 bpsGridiron-124 | AACCGGATATTCATTACCCAATCAGGGCGATGGCCCACTACG (SEQ ID NO. 244) |
| 42 bpsGridiron-125 | CCGTCAATAGATAATACATTTAATCATAAGGGAACCGAACTG (SEQ ID NO. 245) |
| 42 bpsGridiron-126 | ACCAACTTTGAAAGAGGACAGAAAACAGAGGTGAGGCGGTCA (SEQ ID NO. 246) |
| 42 bpsGridiron-127 | ATCAACAATAGATAAGTCCTGTGTCCAGACGACGACAATAAA (SEQ ID NO. 247) |
| 42 bpsGridiron-128 | GCAGAGGCATTTTCGAGCCAGGTATGTTAGCAAACGTAGAAA (SEQ ID NO. 248) |
| 42 bpsGridiron-129 | AGGAAACGCAATAATAACGGATTGCTTTGAATACCAAGTTAC (SEQ ID NO. 249) |
| 42 bpsGridiron-130 | GTCAGATGAATATACAGTAACAAACCAATCAATAATCGGCTG (SEQ ID NO. 250) |
| 42 bpsGridiron-131 | TCCTAATTTACGAGCATGTAGAGTACCTTTTACATCGGGAGA (SEQ ID NO. 251) |
| 42 bpsGridiron-132 | AACAATAACGGATTCGCCTGAATACCCAAAAGAACTGGCATG (SEQ ID NO. 252) |
| 42 bpsGridiron-133 | ATTAAGACTCCTTATTACGCATAATAAGAGAATATAAAGTAC (SEQ ID NO. 253) |
| 42 bpsGridiron-134 | CGACAAAAGGTAAAGTAATTCAACAAGAAAAATAATATCCCA (SEQ ID NO. 254) |
| 42 bpsGridiron-135 | CATTAAACGGGTAAAATACGTTGAGTGAATAACCTTGCTTCT (SEQ ID NO. 255) |
| 42 bpsGridiron-136 | AAAATCGCGCAGAGGCGAATTATGGTTTACCAGCGCCAAAGA (SEQ ID NO. 256) |
| 42 bpsGridiron-137 | ATAAAAGAAACGCAAAGACACCAACGCCAACATGTAATTTAG (SEQ ID NO. 257) |
| 42 bpsGridiron-138 | GTGATAAATAAGGCGTTAAATAGAATACACTAAAACACTCAT (SEQ ID NO. 258) |
| 42 bpsGridiron-139 | ACCTAAAACGAAAGAGGCAAAAAGAATAAACACCGGAATCAT (SEQ ID NO. 259) |

TABLE 2-continued

Sequences of the staples in the 42 bps Gridiron structure

| Name (No.) | Sequence |
|---|---|
| 42 bpsGridiron-140 | AATTACTAGAAAAAGCCTGTTGGATAAGTGCCGTCGAGAGGG (SEQ ID NO. 260) |
| 42 bpsGridiron-141 | GGGTTTTGCTCAGTACCAGGCTAGTATCATATGCGTTATACA (SEQ ID NO. 261) |
| 42 bpsGridiron-142 | TACATTTAACAATTTCATTTGATAGGTGTATCACCGTACTCA (SEQ ID NO. 262) |
| 42 bpsGridiron-143 | TTGATATAAGTATAGCCCGGAAATTACCTTTTTTAATGGAAA (SEQ ID NO. 263) |
| 42 bpsGridiron-144 | AATTCTTACCAGTATAAAGCCGTATTAAGAGGCTGAGACTCC (SEQ ID NO. 264) |
| 42 bpsGridiron-145 | GTGCCCGTATAAACAGTTAATCATCAAGAAAACAAAATTAAT (SEQ ID NO. 265) |
| 42 bpsGridiron-146 | AAAAGAAGATGATGAAACAAAGCCCCCTGCCTATTTCGGAAC (SEQ ID NO. 266) |
| 42 bpsGridiron-147 | CTATTATTCTGAAACATGAAAAACGCTCAACAGTAGGGCTTA (SEQ ID NO. 267) |
| 42 bpsGridiron-148 | ATTGAGAATCGCCATATTTAACACGGAATAAGTTTATTTTGT (SEQ ID NO. 268) |
| 42 bpsGridiron-149 | CACAATCAATAGAAAATTCATATTCATTTCAATTACCTGAGC (SEQ ID NO. 269) |
| 42 bpsGridiron-150 | CAGTACATAAATCAATATATGAATGCCACTACGAAGGCACCA (SEQ ID NO. 270) |
| 42 bpsGridiron-151 | GTAAATCGTCGCTATTAATTAACCTGCTCCATGTTACTTAGC (SEQ ID NO. 271) |
| 42 bpsGridiron-152 | AGCGCGAAACAAAGTACAACGATGGTTTGAAATACCGACCGT (SEQ ID NO. 272) |
| 42 bpsGridiron-153 | TATAACTATATGTAAATGCTGCAAATATCGCGTTTTAATTCG (SEQ ID NO. 273) |
| 42 bpsGridiron-154 | AAGAGGAAGCCCGAAAGACTTATGCAAATCCAATCGCAAGAC (SEQ ID NO. 274) |
| 42 bpsGridiron-155 | TAGTGAATTTATCAAAATCATGGAAGCAAACTCCAACAGGTC (SEQ ID NO. 275) |
| 42 bpsGridiron-156 | AGCTTCAAAGCGAACCAGACCAGGTCTGAGAGACTACCTTTT (SEQ ID NO. 276) |
| 42 bpsGridiron-157 | AAAGAACGCGAGAAAACTTTTCTGACTATTATAGTCAGAAGC (SEQ ID NO. 277) |
| 42 bpsGridiron-158 | CTCAAATGCTTTAAACAGTTCTAAGACGCTGAGAAGAGTCAA (SEQ ID NO. 278) |
| 42 bpsGridiron-159 | AAACATAGCGATAGCTTAGATAGAAAACGAGAATGACCATAA (SEQ ID NO. 279) |
| 42 bpsGridiron-160 | ATCAAAAATCAGGTCTTTACCTCAAATATATTTTAGTTAATT (SEQ ID NO. 280) |
| 42 bpsGridiron-161 | TCATCTTCTGACCTAAATTTAGAGATTTGTATCATCGCCTGA (SEQ ID NO. 281) |
| 42 bpsGridiron-162 | TAAATTGTGTCGAAATCCGCGATTTTCCCTTAGAATCCTTGA (SEQ ID NO. 282) |

The claims are not intended to be limited to the embodiments and examples described herein.

SEQUENCE LISTING

<160> NUMBER OF SEQ ID NOS: 282

<210> SEQ ID NO 1
<211> LENGTH: 42
<212> TYPE: DNA
<213> ORGANISM: Artificial Sequence
<220> FEATURE:
<223> OTHER INFORMATION: Staple Strand

<400> SEQUENCE: 1
gaaaattcat aagtaagcgt catacatggc ttagacggga ga                     42

<210> SEQ ID NO 2
<211> LENGTH: 42
<212> TYPE: DNA
<213> ORGANISM: Artificial Sequence
<220> FEATURE:
<223> OTHER INFORMATION: Staple Strand

```
<400> SEQUENCE: 2
atattcacaa aataaaaaca gggaagcgca ttttgatgat ac                          42

<210> SEQ ID NO 3
<211> LENGTH: 42
<212> TYPE: DNA
<213> ORGANISM: Artificial Sequence
<220> FEATURE:
<223> OTHER INFORMATION: Staple Strand

<400> SEQUENCE: 3
aggagtgtac taataaacag ccatattatt taattggcct tg                          42

<210> SEQ ID NO 4
<211> LENGTH: 42
<212> TYPE: DNA
<213> ORGANISM: Artificial Sequence
<220> FEATURE:
<223> OTHER INFORMATION: Staple Strand

<400> SEQUENCE: 4
gccagttaca aggtaataag ttttaacggg gtgtcctgaa ca                          42

<210> SEQ ID NO 5
<211> LENGTH: 42
<212> TYPE: DNA
<213> ORGANISM: Artificial Sequence
<220> FEATURE:
<223> OTHER INFORMATION: Staple Strand

<400> SEQUENCE: 5
gcagaacgcg cgaggttgag gcaggtcaga cgtcccaatc ca                          42

<210> SEQ ID NO 6
<211> LENGTH: 42
<212> TYPE: DNA
<213> ORGANISM: Artificial Sequence
<220> FEATURE:
<223> OTHER INFORMATION: Staple Strand

<400> SEQUENCE: 6
aataagaaac ggacttgagc catttgggaa ttttcagcta at                          42

<210> SEQ ID NO 7
<211> LENGTH: 42
<212> TYPE: DNA
<213> ORGANISM: Artificial Sequence
<220> FEATURE:
<223> OTHER INFORMATION: Staple Strand

<400> SEQUENCE: 7
gagagaataa ccaaataaat cctcattaaa gcaaagggc ga                           42

<210> SEQ ID NO 8
<211> LENGTH: 42
<212> TYPE: DNA
<213> ORGANISM: Artificial Sequence
<220> FEATURE:
<223> OTHER INFORMATION: Staple Strand

<400> SEQUENCE: 8
agcattgaca gctgtttatc aacaatagat aacagtgcct tg                          42

<210> SEQ ID NO 9
```

<211> LENGTH: 42
<212> TYPE: DNA
<213> ORGANISM: Artificial Sequence
<220> FEATURE:
<223> OTHER INFORMATION: Staple Strand

<400> SEQUENCE: 9
agtaacagtg cccagtaata agagaatata aaagccgccg cc          42

<210> SEQ ID NO 10
<211> LENGTH: 42
<212> TYPE: DNA
<213> ORGANISM: Artificial Sequence
<220> FEATURE:
<223> OTHER INFORMATION: Staple Strand

<400> SEQUENCE: 10
gcattttcga gccgtataaa cagttaatgc cctatcaaaa tc          42

<210> SEQ ID NO 11
<211> LENGTH: 42
<212> TYPE: DNA
<213> ORGANISM: Artificial Sequence
<220> FEATURE:
<223> OTHER INFORMATION: Staple Strand

<400> SEQUENCE: 11
attaagacgc tcgccaccag aaccaccacc aggtaccgac aa          42

<210> SEQ ID NO 12
<211> LENGTH: 42
<212> TYPE: DNA
<213> ORGANISM: Artificial Sequence
<220> FEATURE:
<223> OTHER INFORMATION: Staple Strand

<400> SEQUENCE: 12
aaggtaaagt aagcaccatt accattagca aggatagctt ag          42

<210> SEQ ID NO 13
<211> LENGTH: 44
<212> TYPE: DNA
<213> ORGANISM: Artificial Sequence
<220> FEATURE:
<223> OTHER INFORMATION: Staple Strand

<400> SEQUENCE: 13
tttaccgttc ctggtttacc agcgccaaag accagaatgg aaag          44

<210> SEQ ID NO 14
<211> LENGTH: 42
<212> TYPE: DNA
<213> ORGANISM: Artificial Sequence
<220> FEATURE:
<223> OTHER INFORMATION: Staple Strand

<400> SEQUENCE: 14
cattcaaccg attgacggaa attattcatt aaagccttta ca          42

<210> SEQ ID NO 15
<211> LENGTH: 40
<212> TYPE: DNA
<213> ORGANISM: Artificial Sequence
<220> FEATURE:
<223> OTHER INFORMATION: Staple Strand

<400> SEQUENCE: 15

-continued gaaaatagca ggtgaattat caccgtcacc atttttttgtt       40

<210> SEQ ID NO 16
<211> LENGTH: 42
<212> TYPE: DNA
<213> ORGANISM: Artificial Sequence
<220> FEATURE:
<223> OTHER INFORMATION: Staple Strand

<400> SEQUENCE: 16
gcaaagacac cgtaaatgaa ttttctgtat ggtaattgag cg       42

<210> SEQ ID NO 17
<211> LENGTH: 42
<212> TYPE: DNA
<213> ORGANISM: Artificial Sequence
<220> FEATURE:
<223> OTHER INFORMATION: Staple Strand

<400> SEQUENCE: 17
tagcattcca caccctgaac aaagtcagag gggattttgc ta       42

<210> SEQ ID NO 18
<211> LENGTH: 42
<212> TYPE: DNA
<213> ORGANISM: Artificial Sequence
<220> FEATURE:
<223> OTHER INFORMATION: Staple Strand

<400> SEQUENCE: 18
aacaactttc acgctaacga gcgtctttcc agacaacgcc tg       42

<210> SEQ ID NO 19
<211> LENGTH: 42
<212> TYPE: DNA
<213> ORGANISM: Artificial Sequence
<220> FEATURE:
<223> OTHER INFORMATION: Staple Strand

<400> SEQUENCE: 19
aatcttacca aacagtttca gcggagtgag aaatgtagaa ac       42

<210> SEQ ID NO 20
<211> LENGTH: 42
<212> TYPE: DNA
<213> ORGANISM: Artificial Sequence
<220> FEATURE:
<223> OTHER INFORMATION: Staple Strand

<400> SEQUENCE: 20
agaaaaataa tgtttcgtca ccagtacaaa ctagcctaat tt       42

<210> SEQ ID NO 21
<211> LENGTH: 42
<212> TYPE: DNA
<213> ORGANISM: Artificial Sequence
<220> FEATURE:
<223> OTHER INFORMATION: Staple Strand

<400> SEQUENCE: 21
attaactgaa cagacagccc tcatagttag cgacaatcaa ta       42

<210> SEQ ID NO 22
<211> LENGTH: 40
<212> TYPE: DNA

<213> ORGANISM: Artificial Sequence
<220> FEATURE:
<223> OTHER INFORMATION: Staple Strand

<400> SEQUENCE: 22
aacaacatga gagccagcaa aatcaccagt attctgtcca          40

<210> SEQ ID NO 23
<211> LENGTH: 42
<212> TYPE: DNA
<213> ORGANISM: Artificial Sequence
<220> FEATURE:
<223> OTHER INFORMATION: Staple Strand

<400> SEQUENCE: 23
cgtaacactg aatcccatcc taatttacga gctagaaagg aa        42

<210> SEQ ID NO 24
<211> LENGTH: 42
<212> TYPE: DNA
<213> ORGANISM: Artificial Sequence
<220> FEATURE:
<223> OTHER INFORMATION: Staple Strand

<400> SEQUENCE: 24
caactaaagg attaacaacg ccaacatgta atacccatgt ac        42

<210> SEQ ID NO 25
<211> LENGTH: 42
<212> TYPE: DNA
<213> ORGANISM: Artificial Sequence
<220> FEATURE:
<223> OTHER INFORMATION: Staple Strand

<400> SEQUENCE: 25
aatcgccata tattgcgaat aataattttt tcgcttaggt tg        42

<210> SEQ ID NO 26
<211> LENGTH: 42
<212> TYPE: DNA
<213> ORGANISM: Artificial Sequence
<220> FEATURE:
<223> OTHER INFORMATION: Staple Strand

<400> SEQUENCE: 26
ataggtctga ggggatagca agcccaatag gattaggcag ag        42

<210> SEQ ID NO 27
<211> LENGTH: 44
<212> TYPE: DNA
<213> ORGANISM: Artificial Sequence
<220> FEATURE:
<223> OTHER INFORMATION: Staple Strand

<400> SEQUENCE: 27
tccagacgtt aacggaataa gtttattttg tctaacgatc taaa      44

<210> SEQ ID NO 28
<211> LENGTH: 40
<212> TYPE: DNA
<213> ORGANISM: Artificial Sequence
<220> FEATURE:
<223> OTHER INFORMATION: Staple Strand

<400> SEQUENCE: 28
tcgcccacgc agccattgca acaggaaaaa tgcgccgaca          40

<210> SEQ ID NO 29
<211> LENGTH: 42
<212> TYPE: DNA
<213> ORGANISM: Artificial Sequence
<220> FEATURE:
<223> OTHER INFORMATION: Staple Strand

<400> SEQUENCE: 29
cctcattttc aagactacct ttttaacctc cgacgttgaa aa                42

<210> SEQ ID NO 30
<211> LENGTH: 42
<212> TYPE: DNA
<213> ORGANISM: Artificial Sequence
<220> FEATURE:
<223> OTHER INFORMATION: Staple Strand

<400> SEQUENCE: 30
tctccaaaaa atgaattacc tttttaatg gagagccacc ac                 42

<210> SEQ ID NO 31
<211> LENGTH: 40
<212> TYPE: DNA
<213> ORGANISM: Artificial Sequence
<220> FEATURE:
<223> OTHER INFORMATION: Staple Strand

<400> SEQUENCE: 31
atataagtat ttgacgctca atcgtctgaa gataagtgcc                   40

<210> SEQ ID NO 32
<211> LENGTH: 42
<212> TYPE: DNA
<213> ORGANISM: Artificial Sequence
<220> FEATURE:
<223> OTHER INFORMATION: Staple Strand

<400> SEQUENCE: 32
accctcagag cgagaagagt caatagtgaa ttcctgccta tt                42

<210> SEQ ID NO 33
<211> LENGTH: 42
<212> TYPE: DNA
<213> ORGANISM: Artificial Sequence
<220> FEATURE:
<223> OTHER INFORMATION: Staple Strand

<400> SEQUENCE: 33
tcggaaccta ttgtgagtga ataaccttgc ttcagagcca cc                42

<210> SEQ ID NO 34
<211> LENGTH: 40
<212> TYPE: DNA
<213> ORGANISM: Artificial Sequence
<220> FEATURE:
<223> OTHER INFORMATION: Staple Strand

<400> SEQUENCE: 34
cgtttgccaa ttcaccagtc acacgaccag ttcggtcata                   40

<210> SEQ ID NO 35
<211> LENGTH: 40
<212> TYPE: DNA
<213> ORGANISM: Artificial Sequence
<220> FEATURE:

<223> OTHER INFORMATION: Staple Strand

<400> SEQUENCE: 35
aaacatagcg ccggaaacgt caccaatgaa taattttccc         40

<210> SEQ ID NO 36
<211> LENGTH: 42
<212> TYPE: DNA
<213> ORGANISM: Artificial Sequence
<220> FEATURE:
<223> OTHER INFORMATION: Staple Strand

<400> SEQUENCE: 36
acaatttcat taaggctcca aaaggagcct tttatacttc tg       42

<210> SEQ ID NO 37
<211> LENGTH: 40
<212> TYPE: DNA
<213> ORGANISM: Artificial Sequence
<220> FEATURE:
<223> OTHER INFORMATION: Staple Strand

<400> SEQUENCE: 37
gaacaaagaa tcagtagcga cagaatcaag ttgagtaaca         40

<210> SEQ ID NO 38
<211> LENGTH: 42
<212> TYPE: DNA
<213> ORGANISM: Artificial Sequence
<220> FEATURE:
<223> OTHER INFORMATION: Staple Strand

<400> SEQUENCE: 38
gataatacat ttgctttcga ggtgaatttc ttagccctaa aa       42

<210> SEQ ID NO 39
<211> LENGTH: 40
<212> TYPE: DNA
<213> ORGANISM: Artificial Sequence
<220> FEATURE:
<223> OTHER INFORMATION: Staple Strand

<400> SEQUENCE: 39
acagagatat agcgcgtttt catcggcatt taataaaagg         40

<210> SEQ ID NO 40
<211> LENGTH: 42
<212> TYPE: DNA
<213> ORGANISM: Artificial Sequence
<220> FEATURE:
<223> OTHER INFORMATION: Staple Strand

<400> SEQUENCE: 40
attttaaaag ttttgccttt agcgtcagac tggaacccTT ct       42

<210> SEQ ID NO 41
<211> LENGTH: 42
<212> TYPE: DNA
<213> ORGANISM: Artificial Sequence
<220> FEATURE:
<223> OTHER INFORMATION: Staple Strand

<400> SEQUENCE: 41
gacctgaaag ccggaaccag agccaccacc ggaacgttat ta       42

<210> SEQ ID NO 42
<211> LENGTH: 42
<212> TYPE: DNA
<213> ORGANISM: Artificial Sequence
<220> FEATURE:
<223> OTHER INFORMATION: Staple Strand

<400> SEQUENCE: 42
atcaaaatca cgtaagaata cgtggcacag acggttttgc tc    42

<210> SEQ ID NO 43
<211> LENGTH: 42
<212> TYPE: DNA
<213> ORGANISM: Artificial Sequence
<220> FEATURE:
<223> OTHER INFORMATION: Staple Strand

<400> SEQUENCE: 43
agtaccaggc gatggattat ttacattggc agtcttttca ta    42

<210> SEQ ID NO 44
<211> LENGTH: 42
<212> TYPE: DNA
<213> ORGANISM: Artificial Sequence
<220> FEATURE:
<223> OTHER INFORMATION: Staple Strand

<400> SEQUENCE: 44
aattcgacaa cgagaaggat taggattagc ggaatatttt tg    42

<210> SEQ ID NO 45
<211> LENGTH: 42
<212> TYPE: DNA
<213> ORGANISM: Artificial Sequence
<220> FEATURE:
<223> OTHER INFORMATION: Staple Strand

<400> SEQUENCE: 45
aatggctatt accgtactca ggaggtttag tactttacaa ac    42

<210> SEQ ID NO 46
<211> LENGTH: 42
<212> TYPE: DNA
<213> ORGANISM: Artificial Sequence
<220> FEATURE:
<223> OTHER INFORMATION: Staple Strand

<400> SEQUENCE: 46
taggtgtatc agtctttaat gcgcgaactg ataaacagct tg    42

<210> SEQ ID NO 47
<211> LENGTH: 42
<212> TYPE: DNA
<213> ORGANISM: Artificial Sequence
<220> FEATURE:
<223> OTHER INFORMATION: Staple Strand

<400> SEQUENCE: 47
ataccgatag tcgctcatgg aaatacctac attagcccgg aa    42

<210> SEQ ID NO 48
<211> LENGTH: 42
<212> TYPE: DNA
<213> ORGANISM: Artificial Sequence
<220> FEATURE:
<223> OTHER INFORMATION: Staple Strand

<400> SEQUENCE: 48
gtttatcagc ttgaggattt agaagtatta gaccgccacc ct                42

<210> SEQ ID NO 49
<211> LENGTH: 42
<212> TYPE: DNA
<213> ORGANISM: Artificial Sequence
<220> FEATURE:
<223> OTHER INFORMATION: Staple Strand

<400> SEQUENCE: 49
cagaaccgcc atataatcct gattgtttgg ataattgtat cg                42

<210> SEQ ID NO 50
<211> LENGTH: 42
<212> TYPE: DNA
<213> ORGANISM: Artificial Sequence
<220> FEATURE:
<223> OTHER INFORMATION: Staple Strand

<400> SEQUENCE: 50
agactcctca atcgtattaa atcctttgcc cgaaccgcct cc                42

<210> SEQ ID NO 51
<211> LENGTH: 42
<212> TYPE: DNA
<213> ORGANISM: Artificial Sequence
<220> FEATURE:
<223> OTHER INFORMATION: Staple Strand

<400> SEQUENCE: 51
ctcagagccg ctatcatcat attcctgatt attaagaggc tg                42

<210> SEQ ID NO 52
<211> LENGTH: 42
<212> TYPE: DNA
<213> ORGANISM: Artificial Sequence
<220> FEATURE:
<223> OTHER INFORMATION: Staple Strand

<400> SEQUENCE: 52
tcgctattaa taccatcgat agcagcaccg taaaccacca ga                42

<210> SEQ ID NO 53
<211> LENGTH: 42
<212> TYPE: DNA
<213> ORGANISM: Artificial Sequence
<220> FEATURE:
<223> OTHER INFORMATION: Staple Strand

<400> SEQUENCE: 53
aggagcggaa tcaccctcag aaccgccacc ctctgtaaat cg                42

<210> SEQ ID NO 54
<211> LENGTH: 42
<212> TYPE: DNA
<213> ORGANISM: Artificial Sequence
<220> FEATURE:
<223> OTHER INFORMATION: Staple Strand

<400> SEQUENCE: 54
aaatcaatat atattctgaa acatgaaagt atcagatgat gg                42

<210> SEQ ID NO 55
<211> LENGTH: 42

<212> TYPE: DNA
<213> ORGANISM: Artificial Sequence
<220> FEATURE:
<223> OTHER INFORMATION: Staple Strand

<400> SEQUENCE: 55
caattcatca accctcagaa ccgccaccct caaacagtac at                          42

<210> SEQ ID NO 56
<211> LENGTH: 42
<212> TYPE: DNA
<213> ORGANISM: Artificial Sequence
<220> FEATURE:
<223> OTHER INFORMATION: Staple Strand

<400> SEQUENCE: 56
ggttatataa ccggctacag aggctttgag gacttaattg ag                          42

<210> SEQ ID NO 57
<211> LENGTH: 40
<212> TYPE: DNA
<213> ORGANISM: Artificial Sequence
<220> FEATURE:
<223> OTHER INFORMATION: Staple Strand

<400> SEQUENCE: 57
taaggcgttc ccaattctgc gaacgagtag tgaaataccg                             40

<210> SEQ ID NO 58
<211> LENGTH: 44
<212> TYPE: DNA
<213> ORGANISM: Artificial Sequence
<220> FEATURE:
<223> OTHER INFORMATION: Staple Strand

<400> SEQUENCE: 58
gcttaattgc taacgcaata ataacggaat acaggtcatt tttg                        44

<210> SEQ ID NO 59
<211> LENGTH: 42
<212> TYPE: DNA
<213> ORGANISM: Artificial Sequence
<220> FEATURE:
<223> OTHER INFORMATION: Staple Strand

<400> SEQUENCE: 59
taatttcatc tacttcaaat atcgcgtttt aatcataatt ac                          42

<210> SEQ ID NO 60
<211> LENGTH: 42
<212> TYPE: DNA
<213> ORGANISM: Artificial Sequence
<220> FEATURE:
<223> OTHER INFORMATION: Staple Strand

<400> SEQUENCE: 60
tagaaaaagc cgtttaccag acgacgataa aaatatttta gt                          42

<210> SEQ ID NO 61
<211> LENGTH: 44
<212> TYPE: DNA
<213> ORGANISM: Artificial Sequence
<220> FEATURE:
<223> OTHER INFORMATION: Staple Strand

<400> SEQUENCE: 61
agttgagatt tagactcctt attacgcagt atattattac aggt          44

<210> SEQ ID NO 62
<211> LENGTH: 42
<212> TYPE: DNA
<213> ORGANISM: Artificial Sequence
<220> FEATURE:
<223> OTHER INFORMATION: Staple Strand

<400> SEQUENCE: 62
aagacaaaga ataatcattg tgaattacct tatacaaatt ct            42

<210> SEQ ID NO 63
<211> LENGTH: 42
<212> TYPE: DNA
<213> ORGANISM: Artificial Sequence
<220> FEATURE:
<223> OTHER INFORMATION: Staple Strand

<400> SEQUENCE: 63
taccagtata atccatgtta cttagccgga acatccaatc gc            42

<210> SEQ ID NO 64
<211> LENGTH: 44
<212> TYPE: DNA
<213> ORGANISM: Artificial Sequence
<220> FEATURE:
<223> OTHER INFORMATION: Staple Strand

<400> SEQUENCE: 64
atctttgacc catacataaa ggtggcaaca taggcaaaag aata          44

<210> SEQ ID NO 65
<211> LENGTH: 40
<212> TYPE: DNA
<213> ORGANISM: Artificial Sequence
<220> FEATURE:
<223> OTHER INFORMATION: Staple Strand

<400> SEQUENCE: 65
aaccgaggag aatataatgc tgtagctcaa gccgaacaaa               40

<210> SEQ ID NO 66
<211> LENGTH: 42
<212> TYPE: DNA
<213> ORGANISM: Artificial Sequence
<220> FEATURE:
<223> OTHER INFORMATION: Staple Strand

<400> SEQUENCE: 66
ctaatatcag agcaccaacc taaaacgaaa gataaaagaa ac            42

<210> SEQ ID NO 67
<211> LENGTH: 42
<212> TYPE: DNA
<213> ORGANISM: Artificial Sequence
<220> FEATURE:
<223> OTHER INFORMATION: Staple Strand

<400> SEQUENCE: 67
ccactacgaa ggagataacc cacaagaatt gaaaacaaag ta            42

<210> SEQ ID NO 68
<211> LENGTH: 42
<212> TYPE: DNA
<213> ORGANISM: Artificial Sequence
<220> FEATURE:
<223> OTHER INFORMATION: Staple Strand

<400> SEQUENCE: 68
caacggagat tctatttgc acccagctac aaatacgtaa tg                             42

<210> SEQ ID NO 69
<211> LENGTH: 40
<212> TYPE: DNA
<213> ORGANISM: Artificial Sequence
<220> FEATURE:
<223> OTHER INFORMATION: Staple Strand

<400> SEQUENCE: 69
tagaaggcta agtacggtgt ctggaagttt cccaatagca                               40

<210> SEQ ID NO 70
<211> LENGTH: 42
<212> TYPE: DNA
<213> ORGANISM: Artificial Sequence
<220> FEATURE:
<223> OTHER INFORMATION: Staple Strand

<400> SEQUENCE: 70
caatcaataa tagtttccat taaacgggta aattttatcc tg                            42

<210> SEQ ID NO 71
<211> LENGTH: 42
<212> TYPE: DNA
<213> ORGANISM: Artificial Sequence
<220> FEATURE:
<223> OTHER INFORMATION: Staple Strand

<400> SEQUENCE: 71
tttcatgagg acggctgtct ttccttatca ttgtgtcgaa at                            42

<210> SEQ ID NO 72
<211> LENGTH: 42
<212> TYPE: DNA
<213> ORGANISM: Artificial Sequence
<220> FEATURE:
<223> OTHER INFORMATION: Staple Strand

<400> SEQUENCE: 72
ccgcgacctg cagccaacgc tcaacagtag ggctaaagac tt                            42

<210> SEQ ID NO 73
<211> LENGTH: 42
<212> TYPE: DNA
<213> ORGANISM: Artificial Sequence
<220> FEATURE:
<223> OTHER INFORMATION: Staple Strand

<400> SEQUENCE: 73
aagattagtt gtgtatcatc gcctgataaa ttccaagaac gg                            42

<210> SEQ ID NO 74
<211> LENGTH: 42
<212> TYPE: DNA
<213> ORGANISM: Artificial Sequence
<220> FEATURE:
<223> OTHER INFORMATION: Staple Strand

<400> SEQUENCE: 74
gtattaaacc aattatacca gtcaggacgt tggccttaaa tc                            42

<210> SEQ ID NO 75
<211> LENGTH: 42
<212> TYPE: DNA
<213> ORGANISM: Artificial Sequence
<220> FEATURE:
<223> OTHER INFORMATION: Staple Strand

<400> SEQUENCE: 75
agaactggct cagtaccgca ctcatcgaga acagcaacac ta    42

<210> SEQ ID NO 76
<211> LENGTH: 42
<212> TYPE: DNA
<213> ORGANISM: Artificial Sequence
<220> FEATURE:
<223> OTHER INFORMATION: Staple Strand

<400> SEQUENCE: 76
tcataaccct ctgtttagta tcatatgcgt tatgcgattt ta    42

<210> SEQ ID NO 77
<211> LENGTH: 42
<212> TYPE: DNA
<213> ORGANISM: Artificial Sequence
<220> FEATURE:
<223> OTHER INFORMATION: Staple Strand

<400> SEQUENCE: 77
agcgaacctc cggaattacg aggcatagta agaagcaagc cg    42

<210> SEQ ID NO 78
<211> LENGTH: 42
<212> TYPE: DNA
<213> ORGANISM: Artificial Sequence
<220> FEATURE:
<223> OTHER INFORMATION: Staple Strand

<400> SEQUENCE: 78
tttttatttt cgaccggaag caaactccaa cagaggcgtt tt    42

<210> SEQ ID NO 79
<211> LENGTH: 42
<212> TYPE: DNA
<213> ORGANISM: Artificial Sequence
<220> FEATURE:
<223> OTHER INFORMATION: Staple Strand

<400> SEQUENCE: 79
aaagcgaacc aatcgtagga atcattaccg cgcattccat at    42

<210> SEQ ID NO 80
<211> LENGTH: 42
<212> TYPE: DNA
<213> ORGANISM: Artificial Sequence
<220> FEATURE:
<223> OTHER INFORMATION: Staple Strand

<400> SEQUENCE: 80
aacagttgat taaataagaa taaacaccgg aattcgagct tc    42

<210> SEQ ID NO 81
<211> LENGTH: 42
<212> TYPE: DNA
<213> ORGANISM: Artificial Sequence
<220> FEATURE:
<223> OTHER INFORMATION: Staple Strand

<400> SEQUENCE: 81
atatgcaact atatccggta ttctaagaac gcggtcagga tt                              42

<210> SEQ ID NO 82
<211> LENGTH: 42
<212> TYPE: DNA
<213> ORGANISM: Artificial Sequence
<220> FEATURE:
<223> OTHER INFORMATION: Staple Strand

<400> SEQUENCE: 82
agagagtacc ttttaagaaa agtaagcaga tacatgtttt aa                              42

<210> SEQ ID NO 83
<211> LENGTH: 42
<212> TYPE: DNA
<213> ORGANISM: Artificial Sequence
<220> FEATURE:
<223> OTHER INFORMATION: Staple Strand

<400> SEQUENCE: 83
taacgccaaa acgacttgcg ggaggttttg aaggaagaaa aa                              42

<210> SEQ ID NO 84
<211> LENGTH: 42
<212> TYPE: DNA
<213> ORGANISM: Artificial Sequence
<220> FEATURE:
<223> OTHER INFORMATION: Staple Strand

<400> SEQUENCE: 84
tctacgttaa taagaaacaa tgaaatagca attgcagata ca                              42

<210> SEQ ID NO 85
<211> LENGTH: 42
<212> TYPE: DNA
<213> ORGANISM: Artificial Sequence
<220> FEATURE:
<223> OTHER INFORMATION: Staple Strand

<400> SEQUENCE: 85
gtagaaaata cccagcgatt ataccaagcg cggttaagcc ca                              42

<210> SEQ ID NO 86
<211> LENGTH: 42
<212> TYPE: DNA
<213> ORGANISM: Artificial Sequence
<220> FEATURE:
<223> OTHER INFORMATION: Staple Strand

<400> SEQUENCE: 86
ataataagag caaaacgaac taacggaaca acgttagcaa ac                              42

<210> SEQ ID NO 87
<211> LENGTH: 42
<212> TYPE: DNA
<213> ORGANISM: Artificial Sequence
<220> FEATURE:
<223> OTHER INFORMATION: Staple Strand

<400> SEQUENCE: 87
tggcatgatt aaggaatacc acattcaact aaagctatct ta                              42

<210> SEQ ID NO 88

```
<210> SEQ ID NO 88
<211> LENGTH: 42
<212> TYPE: DNA
<213> ORGANISM: Artificial Sequence
<220> FEATURE:
<223> OTHER INFORMATION: Staple Strand

<400> SEQUENCE: 88
ccgaagccct tttaattgct ccttttgata agccaaaaga ac        42

<210> SEQ ID NO 89
<211> LENGTH: 42
<212> TYPE: DNA
<213> ORGANISM: Artificial Sequence
<220> FEATURE:
<223> OTHER INFORMATION: Staple Strand

<400> SEQUENCE: 89
aagcccgaaa gtctgaccta aatttaatgg ttatttagtt tg        42

<210> SEQ ID NO 90
<211> LENGTH: 42
<212> TYPE: DNA
<213> ORGANISM: Artificial Sequence
<220> FEATURE:
<223> OTHER INFORMATION: Staple Strand

<400> SEQUENCE: 90
accattagat agattgcttt gaataccaag ttgattaaga gg        42

<210> SEQ ID NO 91
<211> LENGTH: 40
<212> TYPE: DNA
<213> ORGANISM: Artificial Sequence
<220> FEATURE:
<223> OTHER INFORMATION: Staple Strand

<400> SEQUENCE: 91
taaacagttt ttgattagta ataacatcac cattgaatcc        40

<210> SEQ ID NO 92
<211> LENGTH: 42
<212> TYPE: DNA
<213> ORGANISM: Artificial Sequence
<220> FEATURE:
<223> OTHER INFORMATION: Staple Strand

<400> SEQUENCE: 92
aatttcaact tcgcgagaaa acttttttcaa ataccaaaat ag        42

<210> SEQ ID NO 93
<211> LENGTH: 42
<212> TYPE: DNA
<213> ORGANISM: Artificial Sequence
<220> FEATURE:
<223> OTHER INFORMATION: Staple Strand

<400> SEQUENCE: 93
cgagaggctt tttattcatt tcaattacct gagagatggt tt        42

<210> SEQ ID NO 94
<211> LENGTH: 40
<212> TYPE: DNA
<213> ORGANISM: Artificial Sequence
<220> FEATURE:
<223> OTHER INFORMATION: Staple Strand

<400> SEQUENCE: 94
```
attcattaca actatcggcc ttgctggtaa agtaatcttg         40

<210> SEQ ID NO 95
<211> LENGTH: 42
<212> TYPE: DNA
<213> ORGANISM: Artificial Sequence
<220> FEATURE:
<223> OTHER INFORMATION: Staple Strand

<400> SEQUENCE: 95
gagggtagca atatatgtaa atgctgatgc aagaggcgca ga         42

<210> SEQ ID NO 96
<211> LENGTH: 42
<212> TYPE: DNA
<213> ORGANISM: Artificial Sequence
<220> FEATURE:
<223> OTHER INFORMATION: Staple Strand

<400> SEQUENCE: 96
cggtcaatca taacatcaag aaaacaaaat tagcatcgga ac         42

<210> SEQ ID NO 97
<211> LENGTH: 40
<212> TYPE: DNA
<213> ORGANISM: Artificial Sequence
<220> FEATURE:
<223> OTHER INFORMATION: Staple Strand

<400> SEQUENCE: 97
gattcgcctc atttcgcaaa tggtcaataa ttacatcggg         40

<210> SEQ ID NO 98
<211> LENGTH: 42
<212> TYPE: DNA
<213> ORGANISM: Artificial Sequence
<220> FEATURE:
<223> OTHER INFORMATION: Staple Strand

<400> SEQUENCE: 98
aataatggaa gcaccctcag cagcgaaaga caattacatt ta         42

<210> SEQ ID NO 99
<211> LENGTH: 42
<212> TYPE: DNA
<213> ORGANISM: Artificial Sequence
<220> FEATURE:
<223> OTHER INFORMATION: Staple Strand

<400> SEQUENCE: 99
tgcgggatcg tggttagaac ctaccatatc aatttgaaag ag         42

<210> SEQ ID NO 100
<211> LENGTH: 42
<212> TYPE: DNA
<213> ORGANISM: Artificial Sequence
<220> FEATURE:
<223> OTHER INFORMATION: Staple Strand

<400> SEQUENCE: 100
gacagatgaa cactaacaac taatagatta gaaggccgct tt         42

<210> SEQ ID NO 101
<211> LENGTH: 40
<212> TYPE: DNA

```
<213> ORGANISM: Artificial Sequence
<220> FEATURE:
<223> OTHER INFORMATION: Staple Strand

<400> SEQUENCE: 101
ctcaaatatt tggggcgcga gctgaaaagg tctaaagcat                                40

<210> SEQ ID NO 102
<211> LENGTH: 42
<212> TYPE: DNA
<213> ORGANISM: Artificial Sequence
<220> FEATURE:
<223> OTHER INFORMATION: Staple Strand

<400> SEQUENCE: 102
catcgccatt actgaggctt gcagggagtt aagccgtcaa ta                            42

<210> SEQ ID NO 103
<211> LENGTH: 42
<212> TYPE: DNA
<213> ORGANISM: Artificial Sequence
<220> FEATURE:
<223> OTHER INFORMATION: Staple Strand

<400> SEQUENCE: 103
atattcggtc gaaataccg aacgaaccac caggctggct ga                             42

<210> SEQ ID NO 104
<211> LENGTH: 42
<212> TYPE: DNA
<213> ORGANISM: Artificial Sequence
<220> FEATURE:
<223> OTHER INFORMATION: Staple Strand

<400> SEQUENCE: 104
ccttcatcaa gtatccagaa caatattacc gccataaccg at                            42

<210> SEQ ID NO 105
<211> LENGTH: 42
<212> TYPE: DNA
<213> ORGANISM: Artificial Sequence
<220> FEATURE:
<223> OTHER INFORMATION: Staple Strand

<400> SEQUENCE: 105
tctttaggag cggtgtacag accaggcgca tagcagaaga ta                            42

<210> SEQ ID NO 106
<211> LENGTH: 42
<212> TYPE: DNA
<213> ORGANISM: Artificial Sequence
<220> FEATURE:
<223> OTHER INFORMATION: Staple Strand

<400> SEQUENCE: 106
aaacagaggt ggctcattca gtgaataagg ctatctaaaa ta                            42

<210> SEQ ID NO 107
<211> LENGTH: 42
<212> TYPE: DNA
<213> ORGANISM: Artificial Sequence
<220> FEATURE:
<223> OTHER INFORMATION: Staple Strand

<400> SEQUENCE: 107
gtaacaaagc taggcggtca gtattaacac cgtgcggaat cg                            42
```

<210> SEQ ID NO 108
<211> LENGTH: 42
<212> TYPE: DNA
<213> ORGANISM: Artificial Sequence
<220> FEATURE:
<223> OTHER INFORMATION: Staple Strand

<400> SEQUENCE: 108
tcataaatat tttgcctgag tagaagaact caccaaatca ac                            42

<210> SEQ ID NO 109
<211> LENGTH: 42
<212> TYPE: DNA
<213> ORGANISM: Artificial Sequence
<220> FEATURE:
<223> OTHER INFORMATION: Staple Strand

<400> SEQUENCE: 109
aaatcaacag tagactggat agcgtccaat accctgcaac ag                            42

<210> SEQ ID NO 110
<211> LENGTH: 42
<212> TYPE: DNA
<213> ORGANISM: Artificial Sequence
<220> FEATURE:
<223> OTHER INFORMATION: Staple Strand

<400> SEQUENCE: 110
tgccacgctg aaatcaaaaa tcaggtcttt acgtcagttg gc                            42

<210> SEQ ID NO 111
<211> LENGTH: 42
<212> TYPE: DNA
<213> ORGANISM: Artificial Sequence
<220> FEATURE:
<223> OTHER INFORMATION: Staple Strand

<400> SEQUENCE: 111
gaatgaccat agagccagca gcaaatgaaa aatggcatca at                            42

<210> SEQ ID NO 112
<211> LENGTH: 42
<212> TYPE: DNA
<213> ORGANISM: Artificial Sequence
<220> FEATURE:
<223> OTHER INFORMATION: Staple Strand

<400> SEQUENCE: 112
tctactaata gtaaccgttg tagcaatact tccagaaaac ga                            42

<210> SEQ ID NO 113
<211> LENGTH: 42
<212> TYPE: DNA
<213> ORGANISM: Artificial Sequence
<220> FEATURE:
<223> OTHER INFORMATION: Staple Strand

<400> SEQUENCE: 113
tatattttca tcaaaccctc aatcaatatc tgcctgacta tt                            42

<210> SEQ ID NO 114
<211> LENGTH: 42
<212> TYPE: DNA
<213> ORGANISM: Artificial Sequence
<220> FEATURE:

<223> OTHER INFORMATION: Staple Strand

<400> SEQUENCE: 114
atagtcagaa gaatatacag taacagtacc ttcctgttta gc          42

<210> SEQ ID NO 115
<211> LENGTH: 42
<212> TYPE: DNA
<213> ORGANISM: Artificial Sequence
<220> FEATURE:
<223> OTHER INFORMATION: Staple Strand

<400> SEQUENCE: 115
gtaaaatgtt ttgaaaggaa ttgaggaagg tttgccctga cg          42

<210> SEQ ID NO 116
<211> LENGTH: 42
<212> TYPE: DNA
<213> ORGANISM: Artificial Sequence
<220> FEATURE:
<223> OTHER INFORMATION: Staple Strand

<400> SEQUENCE: 116
agaaacacca gaaataaaga aattgcgtag atgggggtaa ta          42

<210> SEQ ID NO 117
<211> LENGTH: 42
<212> TYPE: DNA
<213> ORGANISM: Artificial Sequence
<220> FEATURE:
<223> OTHER INFORMATION: Staple Strand

<400> SEQUENCE: 117
atgatgaaac aaagggaacc gaactgacca acaattattt gc          42

<210> SEQ ID NO 118
<211> LENGTH: 42
<212> TYPE: DNA
<213> ORGANISM: Artificial Sequence
<220> FEATURE:
<223> OTHER INFORMATION: Staple Strand

<400> SEQUENCE: 118
acgtaaaaca gaacgagtag taaattgggc ttgcaaaaga ag          42

<210> SEQ ID NO 119
<211> LENGTH: 42
<212> TYPE: DNA
<213> ORGANISM: Artificial Sequence
<220> FEATURE:
<223> OTHER INFORMATION: Staple Strand

<400> SEQUENCE: 119
gcagaggcga atgcaaaaga agttttgcca gatttcaggt tt          42

<210> SEQ ID NO 120
<211> LENGTH: 42
<212> TYPE: DNA
<213> ORGANISM: Artificial Sequence
<220> FEATURE:
<223> OTHER INFORMATION: Staple Strand

<400> SEQUENCE: 120
aacgtcagat gcaaagcgga ttgcatcaaa aacaaaatc gc          42

<210> SEQ ID NO 121
<211> LENGTH: 42
<212> TYPE: DNA
<213> ORGANISM: Artificial Sequence
<220> FEATURE:
<223> OTHER INFORMATION: Staple Strand

<400> SEQUENCE: 121
cctcccgact tgcgggaggt tctgcattaa tgaatcggcc aa         42

<210> SEQ ID NO 122
<211> LENGTH: 42
<212> TYPE: DNA
<213> ORGANISM: Artificial Sequence
<220> FEATURE:
<223> OTHER INFORMATION: Staple Strand

<400> SEQUENCE: 122
taactcacat taattgcgtt gagaattaac tgaacaccct ga         42

<210> SEQ ID NO 123
<211> LENGTH: 42
<212> TYPE: DNA
<213> ORGANISM: Artificial Sequence
<220> FEATURE:
<223> OTHER INFORMATION: Staple Strand

<400> SEQUENCE: 123
aaaatgaaaa tagcagcctt tttaaatttt tgttaaatca gc         42

<210> SEQ ID NO 124
<211> LENGTH: 42
<212> TYPE: DNA
<213> ORGANISM: Artificial Sequence
<220> FEATURE:
<223> OTHER INFORMATION: Staple Strand

<400> SEQUENCE: 124
aacaggaaga ttgtataagc atacaatttt atcctgaatc tt         42

<210> SEQ ID NO 125
<211> LENGTH: 42
<212> TYPE: DNA
<213> ORGANISM: Artificial Sequence
<220> FEATURE:
<223> OTHER INFORMATION: Staple Strand

<400> SEQUENCE: 125
agttgctatt ttgcacccag caatatttaa attgtaaacg tt         42

<210> SEQ ID NO 126
<211> LENGTH: 42
<212> TYPE: DNA
<213> ORGANISM: Artificial Sequence
<220> FEATURE:
<223> OTHER INFORMATION: Staple Strand

<400> SEQUENCE: 126
aatattttgt taaaattcgc aacagagaga ataacataaa aa         42

<210> SEQ ID NO 127
<211> LENGTH: 42
<212> TYPE: DNA
<213> ORGANISM: Artificial Sequence
<220> FEATURE:
<223> OTHER INFORMATION: Staple Strand

<400> SEQUENCE: 127
cagggaagcg cattagacgg gcgctcactg cccgctttcc ag                              42

<210> SEQ ID NO 128
<211> LENGTH: 42
<212> TYPE: DNA
<213> ORGANISM: Artificial Sequence
<220> FEATURE:
<223> OTHER INFORMATION: Staple Strand

<400> SEQUENCE: 128
tcgggaaacc tgtcgtgcca gttgaagcct taaatcaaga tt                              42

<210> SEQ ID NO 129
<211> LENGTH: 42
<212> TYPE: DNA
<213> ORGANISM: Artificial Sequence
<220> FEATURE:
<223> OTHER INFORMATION: Staple Strand

<400> SEQUENCE: 129
accaacgcta acgagcgtct ttgtcaatca tatgtacccc gg                              42

<210> SEQ ID NO 130
<211> LENGTH: 42
<212> TYPE: DNA
<213> ORGANISM: Artificial Sequence
<220> FEATURE:
<223> OTHER INFORMATION: Staple Strand

<400> SEQUENCE: 130
ggtcattgcc tgagagtctg gacgattttt tgtttaacgt ca                              42

<210> SEQ ID NO 131
<211> LENGTH: 42
<212> TYPE: DNA
<213> ORGANISM: Artificial Sequence
<220> FEATURE:
<223> OTHER INFORMATION: Staple Strand

<400> SEQUENCE: 131
ttatcccaat ccaaataaga aagcaaacaa gagaatcgat ga                              42

<210> SEQ ID NO 132
<211> LENGTH: 42
<212> TYPE: DNA
<213> ORGANISM: Artificial Sequence
<220> FEATURE:
<223> OTHER INFORMATION: Staple Strand

<400> SEQUENCE: 132
acggtaatcg taaaactagc atccagagcc taatttgcca gt                              42

<210> SEQ ID NO 133
<211> LENGTH: 42
<212> TYPE: DNA
<213> ORGANISM: Artificial Sequence
<220> FEATURE:
<223> OTHER INFORMATION: Staple Strand

<400> SEQUENCE: 133
ccgccaccct cagagccacc atttcatcaa cattaaatgt ga                              42

<210> SEQ ID NO 134
<211> LENGTH: 42

<212> TYPE: DNA
<213> ORGANISM: Artificial Sequence
<220> FEATURE:
<223> OTHER INFORMATION: Staple Strand

<400> SEQUENCE: 134
tcatttttta accaatagga agtagcgcgt tttcatcggc at                            42

<210> SEQ ID NO 135
<211> LENGTH: 42
<212> TYPE: DNA
<213> ORGANISM: Artificial Sequence
<220> FEATURE:
<223> OTHER INFORMATION: Staple Strand

<400> SEQUENCE: 135
aaccatcgat agcagcaccg ttggggtgcc taatgagtga gc                            42

<210> SEQ ID NO 136
<211> LENGTH: 42
<212> TYPE: DNA
<213> ORGANISM: Artificial Sequence
<220> FEATURE:
<223> OTHER INFORMATION: Staple Strand

<400> SEQUENCE: 136
agcttgcatg cctgcaggtc gtagttgcgc cgacaatgac aa                            42

<210> SEQ ID NO 137
<211> LENGTH: 42
<212> TYPE: DNA
<213> ORGANISM: Artificial Sequence
<220> FEATURE:
<223> OTHER INFORMATION: Staple Strand

<400> SEQUENCE: 137
tttcggtcat agcccccctta tagagatcta caaaggctat ca                           42

<210> SEQ ID NO 138
<211> LENGTH: 42
<212> TYPE: DNA
<213> ORGANISM: Artificial Sequence
<220> FEATURE:
<223> OTHER INFORMATION: Staple Strand

<400> SEQUENCE: 138
cctcatatat tttaaatgca aaaaaaggc tccaaaagga gc                             42

<210> SEQ ID NO 139
<211> LENGTH: 42
<212> TYPE: DNA
<213> ORGANISM: Artificial Sequence
<220> FEATURE:
<223> OTHER INFORMATION: Staple Strand

<400> SEQUENCE: 139
tttcacgttg aaaatctcca atgcctgagt aatgtgtagg ta                            42

<210> SEQ ID NO 140
<211> LENGTH: 42
<212> TYPE: DNA
<213> ORGANISM: Artificial Sequence
<220> FEATURE:
<223> OTHER INFORMATION: Staple Strand

<400> SEQUENCE: 140
aagattcaaa agggtgagaa atgagaatag aaaggaacaa ct                         42

<210> SEQ ID NO 141
<211> LENGTH: 42
<212> TYPE: DNA
<213> ORGANISM: Artificial Sequence
<220> FEATURE:
<223> OTHER INFORMATION: Staple Strand

<400> SEQUENCE: 141
tcatagttag cgtaacgatc ttggtcatag ctgtttcctg tg                         42

<210> SEQ ID NO 142
<211> LENGTH: 42
<212> TYPE: DNA
<213> ORGANISM: Artificial Sequence
<220> FEATURE:
<223> OTHER INFORMATION: Staple Strand

<400> SEQUENCE: 142
ccgagctcga attcgtaatc aaaagttttg tcgtctttcc ag                         42

<210> SEQ ID NO 143
<211> LENGTH: 42
<212> TYPE: DNA
<213> ORGANISM: Artificial Sequence
<220> FEATURE:
<223> OTHER INFORMATION: Staple Strand

<400> SEQUENCE: 143
acgttagtaa atgaattttc ttctccgtgg gaacaaacgg cg                         42

<210> SEQ ID NO 144
<211> LENGTH: 42
<212> TYPE: DNA
<213> ORGANISM: Artificial Sequence
<220> FEATURE:
<223> OTHER INFORMATION: Staple Strand

<400> SEQUENCE: 144
gcgagtaaca acccgtcgga tgtatgggat tttgctaaac aa                         42

<210> SEQ ID NO 145
<211> LENGTH: 42
<212> TYPE: DNA
<213> ORGANISM: Artificial Sequence
<220> FEATURE:
<223> OTHER INFORMATION: Staple Strand

<400> SEQUENCE: 145
ctttaattgt atcggtttat ctcacgttgg tgtagatggg cg                         42

<210> SEQ ID NO 146
<211> LENGTH: 42
<212> TYPE: DNA
<213> ORGANISM: Artificial Sequence
<220> FEATURE:
<223> OTHER INFORMATION: Staple Strand

<400> SEQUENCE: 146
gattgaccgt aatgggatag gagcttgctt tcgaggtgaa tt                         42

<210> SEQ ID NO 147
<211> LENGTH: 42
<212> TYPE: DNA
<213> ORGANISM: Artificial Sequence
<220> FEATURE:
<223> OTHER INFORMATION: Staple Strand

<400> SEQUENCE: 147
ctttcaacag tttcagcgga gggccggaga cagtcaaatc ac                              42

<210> SEQ ID NO 148
<211> LENGTH: 42
<212> TYPE: DNA
<213> ORGANISM: Artificial Sequence
<220> FEATURE:
<223> OTHER INFORMATION: Staple Strand

<400> SEQUENCE: 148
catcaatatg atattcaacc gtcagagccg ccaccctcag aa                              42

<210> SEQ ID NO 149
<211> LENGTH: 42
<212> TYPE: DNA
<213> ORGANISM: Artificial Sequence
<220> FEATURE:
<223> OTHER INFORMATION: Staple Strand

<400> SEQUENCE: 149
ccaccaccgg aaccgcctcc cttctagctg ataaattaat gc                              42

<210> SEQ ID NO 150
<211> LENGTH: 42
<212> TYPE: DNA
<213> ORGANISM: Artificial Sequence
<220> FEATURE:
<223> OTHER INFORMATION: Staple Strand

<400> SEQUENCE: 150
tgaaattgtt atccgctcac agcattgaca ggaggttgag gc                              42

<210> SEQ ID NO 151
<211> LENGTH: 42
<212> TYPE: DNA
<213> ORGANISM: Artificial Sequence
<220> FEATURE:
<223> OTHER INFORMATION: Staple Strand

<400> SEQUENCE: 151
ccaccaccag agccgccgcc aattccacac aacatacgag cc                              42

<210> SEQ ID NO 152
<211> LENGTH: 42
<212> TYPE: DNA
<213> ORGANISM: Artificial Sequence
<220> FEATURE:
<223> OTHER INFORMATION: Staple Strand

<400> SEQUENCE: 152
tctggccttc ctgtagccag cccctcagag ccgccaccag aa                              42

<210> SEQ ID NO 153
<211> LENGTH: 42
<212> TYPE: DNA
<213> ORGANISM: Artificial Sequence
<220> FEATURE:
<223> OTHER INFORMATION: Staple Strand

<400> SEQUENCE: 153
cggagagggt agctattttt gtagcgtttg ccatcttttc at                              42

<210> SEQ ID NO 154
<211> LENGTH: 42
<212> TYPE: DNA
<213> ORGANISM: Artificial Sequence
<220> FEATURE:
<223> OTHER INFORMATION: Staple Strand

<400> SEQUENCE: 154
tcttaaacag cttgataccg aactctagag gatccccggg ta                              42

<210> SEQ ID NO 155
<211> LENGTH: 42
<212> TYPE: DNA
<213> ORGANISM: Artificial Sequence
<220> FEATURE:
<223> OTHER INFORMATION: Staple Strand

<400> SEQUENCE: 155
ggaagcataa agtgtaaagc caatcagtag cgacagaatc aa                              42

<210> SEQ ID NO 156
<211> LENGTH: 42
<212> TYPE: DNA
<213> ORGANISM: Artificial Sequence
<220> FEATURE:
<223> OTHER INFORMATION: Staple Strand

<400> SEQUENCE: 156
gtttgccttt agcgtcagac tcgccatcaa aaataattcg cg                              42

<210> SEQ ID NO 157
<211> LENGTH: 42
<212> TYPE: DNA
<213> ORGANISM: Artificial Sequence
<220> FEATURE:
<223> OTHER INFORMATION: Staple Strand

<400> SEQUENCE: 157
acaggtagaa agattcatca gactccagcc agctttccgg ca                              42

<210> SEQ ID NO 158
<211> LENGTH: 42
<212> TYPE: DNA
<213> ORGANISM: Artificial Sequence
<220> FEATURE:
<223> OTHER INFORMATION: Staple Strand

<400> SEQUENCE: 158
catcgtaacc gtgcatctgc ctggtttaat ttcaacttta at                              42

<210> SEQ ID NO 159
<211> LENGTH: 42
<212> TYPE: DNA
<213> ORGANISM: Artificial Sequence
<220> FEATURE:
<223> OTHER INFORMATION: Staple Strand

<400> SEQUENCE: 159
attcagtgaa taaggcttgc cgtaaaacga cggccagtgc ca                              42

<210> SEQ ID NO 160
<211> LENGTH: 42
<212> TYPE: DNA
<213> ORGANISM: Artificial Sequence
<220> FEATURE:
<223> OTHER INFORMATION: Staple Strand

<400> SEQUENCE: 160
cattgtgaat taccttatgc gaaggataaa aatttttaga ac                              42

<210> SEQ ID NO 161
<211> LENGTH: 42
<212> TYPE: DNA
<213> ORGANISM: Artificial Sequence
<220> FEATURE:
<223> OTHER INFORMATION: Staple Strand

<400> SEQUENCE: 161
tagcaaaatt aagcaataaa gtctactaat agtagtagca tt                              42

<210> SEQ ID NO 162
<211> LENGTH: 42
<212> TYPE: DNA
<213> ORGANISM: Artificial Sequence
<220> FEATURE:
<223> OTHER INFORMATION: Staple Strand

<400> SEQUENCE: 162
cgaacgagta gatttagttt gcgctattac gccagctggc ga                              42

<210> SEQ ID NO 163
<211> LENGTH: 42
<212> TYPE: DNA
<213> ORGANISM: Artificial Sequence
<220> FEATURE:
<223> OTHER INFORMATION: Staple Strand

<400> SEQUENCE: 163
ggcgatcggt gcgggcctct taccattaga tacatttcgc aa                              42

<210> SEQ ID NO 164
<211> LENGTH: 42
<212> TYPE: DNA
<213> ORGANISM: Artificial Sequence
<220> FEATURE:
<223> OTHER INFORMATION: Staple Strand

<400> SEQUENCE: 164
atggtcaata acctgtttag caggcaaagc gccattcgcc at                              42

<210> SEQ ID NO 165
<211> LENGTH: 42
<212> TYPE: DNA
<213> ORGANISM: Artificial Sequence
<220> FEATURE:
<223> OTHER INFORMATION: Staple Strand

<400> SEQUENCE: 165
ccgcttctgg tgccggaaac ctatattttc atttggggcg cg                              42

<210> SEQ ID NO 166
<211> LENGTH: 42
<212> TYPE: DNA
<213> ORGANISM: Artificial Sequence
<220> FEATURE:
<223> OTHER INFORMATION: Staple Strand

<400> SEQUENCE: 166
agctgaaaag gtggcatcaa tcctcagagc ataaagctaa at                              42

<210> SEQ ID NO 167

```
<211> LENGTH: 42
<212> TYPE: DNA
<213> ORGANISM: Artificial Sequence
<220> FEATURE:
<223> OTHER INFORMATION: Staple Strand

<400> SEQUENCE: 167
cggttgtacc aaaaacatta taactaacgg aacaacatta tt                          42

<210> SEQ ID NO 168
<211> LENGTH: 42
<212> TYPE: DNA
<213> ORGANISM: Artificial Sequence
<220> FEATURE:
<223> OTHER INFORMATION: Staple Strand

<400> SEQUENCE: 168
aaaatctacg ttaataaaac ggaccctgta atacttttgc gg                          42

<210> SEQ ID NO 169
<211> LENGTH: 42
<212> TYPE: DNA
<213> ORGANISM: Artificial Sequence
<220> FEATURE:
<223> OTHER INFORMATION: Staple Strand

<400> SEQUENCE: 169 aaggggatg tgctgcaagg cacgccaaaa ggaattacga gg                           42

<210> SEQ ID NO 170
<211> LENGTH: 42
<212> TYPE: DNA
<213> ORGANISM: Artificial Sequence
<220> FEATURE:
<223> OTHER INFORMATION: Staple Strand

<400> SEQUENCE: 170
ttcaactaat gcagatacat agattaagtt gggtaacgcc ag                          42

<210> SEQ ID NO 171
<211> LENGTH: 42
<212> TYPE: DNA
<213> ORGANISM: Artificial Sequence
<220> FEATURE:
<223> OTHER INFORMATION: Staple Strand

<400> SEQUENCE: 171
tatcggcctc aggaagatcg cttgagattt aggaatacca ca                          42

<210> SEQ ID NO 172
<211> LENGTH: 42
<212> TYPE: DNA
<213> ORGANISM: Artificial Sequence
<220> FEATURE:
<223> OTHER INFORMATION: Staple Strand

<400> SEQUENCE: 172
gagaagcctt tatttcaacg cattttaaga actggctcat ta                          42

<210> SEQ ID NO 173
<211> LENGTH: 42
<212> TYPE: DNA
<213> ORGANISM: Artificial Sequence
<220> FEATURE:
<223> OTHER INFORMATION: Staple Strand

<400> SEQUENCE: 173
```
ggttttccca gtcacgacgt tctgacgaga aacaccagaa cg                              42

<210> SEQ ID NO 174
<211> LENGTH: 42
<212> TYPE: DNA
<213> ORGANISM: Artificial Sequence
<220> FEATURE:
<223> OTHER INFORMATION: Staple Strand

<400> SEQUENCE: 174
agtagtaaat tgggcttgag aagtttgagg ggacgacgac ag                              42

<210> SEQ ID NO 175
<211> LENGTH: 42
<212> TYPE: DNA
<213> ORGANISM: Artificial Sequence
<220> FEATURE:
<223> OTHER INFORMATION: Staple Strand

<400> SEQUENCE: 175
tctttcctta tcattccaag acgtaaaaca gaaataaaga aa                              42

<210> SEQ ID NO 176
<211> LENGTH: 42
<212> TYPE: DNA
<213> ORGANISM: Artificial Sequence
<220> FEATURE:
<223> OTHER INFORMATION: Staple Strand

<400> SEQUENCE: 176
ttgtttggat tatacttctg aaaagttacc agaaggaaac cg                              42

<210> SEQ ID NO 177
<211> LENGTH: 42
<212> TYPE: DNA
<213> ORGANISM: Artificial Sequence
<220> FEATURE:
<223> OTHER INFORMATION: Staple Strand

<400> SEQUENCE: 177
aatgaaatag caatagctat caatggatta tttacattgg ca                              42

<210> SEQ ID NO 178
<211> LENGTH: 42
<212> TYPE: DNA
<213> ORGANISM: Artificial Sequence
<220> FEATURE:
<223> OTHER INFORMATION: Staple Strand

<400> SEQUENCE: 178
ccagccattg caacaggaaa agccgttttt attttcatcg ta                              42

<210> SEQ ID NO 179
<211> LENGTH: 42
<212> TYPE: DNA
<213> ORGANISM: Artificial Sequence
<220> FEATURE:
<223> OTHER INFORMATION: Staple Strand

<400> SEQUENCE: 179
gcactcatcg agaacaagca aacgctcatg gaaataccta ca                              42

<210> SEQ ID NO 180
<211> LENGTH: 42
<212> TYPE: DNA

<213> ORGANISM: Artificial Sequence
<220> FEATURE:
<223> OTHER INFORMATION: Staple Strand

<400> SEQUENCE: 180
ttttgacgct caatcgtctg attaccgaag ccctttttaa ga    42

<210> SEQ ID NO 181
<211> LENGTH: 42
<212> TYPE: DNA
<213> ORGANISM: Artificial Sequence
<220> FEATURE:
<223> OTHER INFORMATION: Staple Strand

<400> SEQUENCE: 181
aaagtaagca gatagccgaa cataatggaa gggttagaac ct    42

<210> SEQ ID NO 182
<211> LENGTH: 42
<212> TYPE: DNA
<213> ORGANISM: Artificial Sequence
<220> FEATURE:
<223> OTHER INFORMATION: Staple Strand

<400> SEQUENCE: 182
accatatcaa aattatttgc aacgggtatt aaaccaagta cc    42

<210> SEQ ID NO 183
<211> LENGTH: 42
<212> TYPE: DNA
<213> ORGANISM: Artificial Sequence
<220> FEATURE:
<223> OTHER INFORMATION: Staple Strand

<400> SEQUENCE: 183
ggaatcatta ccgcgcccaa ttcaaactat cggccttgct gg    42

<210> SEQ ID NO 184
<211> LENGTH: 42
<212> TYPE: DNA
<213> ORGANISM: Artificial Sequence
<220> FEATURE:
<223> OTHER INFORMATION: Staple Strand

<400> SEQUENCE: 184
aattaaccgt tgtagcaata cccaataata agagcaagaa ac    42

<210> SEQ ID NO 185
<211> LENGTH: 42
<212> TYPE: DNA
<213> ORGANISM: Artificial Sequence
<220> FEATURE:
<223> OTHER INFORMATION: Staple Strand

<400> SEQUENCE: 185
acaaagtcag agggtaattg accgcctggc cctgagagag tt    42

<210> SEQ ID NO 186
<211> LENGTH: 42
<212> TYPE: DNA
<213> ORGANISM: Artificial Sequence
<220> FEATURE:
<223> OTHER INFORMATION: Staple Strand

<400> SEQUENCE: 186
tattgggcgc cagggtggtt taacgcgagg cgttttagcg aa    42

<210> SEQ ID NO 187
<211> LENGTH: 42
<212> TYPE: DNA
<213> ORGANISM: Artificial Sequence
<220> FEATURE:
<223> OTHER INFORMATION: Staple Strand

<400> SEQUENCE: 187
aggcttatcc ggtattctaa gttcttttca ccagtgagac gg                     42

<210> SEQ ID NO 188
<211> LENGTH: 42
<212> TYPE: DNA
<213> ORGANISM: Artificial Sequence
<220> FEATURE:
<223> OTHER INFORMATION: Staple Strand

<400> SEQUENCE: 188
gcaacagctg attgcccttc agcgctaata tcagagagat aa                     42

<210> SEQ ID NO 189
<211> LENGTH: 42
<212> TYPE: DNA
<213> ORGANISM: Artificial Sequence
<220> FEATURE:
<223> OTHER INFORMATION: Staple Strand

<400> SEQUENCE: 189
cccacaagaa ttgagttaag cttctttgat tagtaataac at                     42

<210> SEQ ID NO 190
<211> LENGTH: 42
<212> TYPE: DNA
<213> ORGANISM: Artificial Sequence
<220> FEATURE:
<223> OTHER INFORMATION: Staple Strand

<400> SEQUENCE: 190
cacttgcctg agtagaagaa cagcaagcaa atcagatata ga                     42

<210> SEQ ID NO 191
<211> LENGTH: 42
<212> TYPE: DNA
<213> ORGANISM: Artificial Sequence
<220> FEATURE:
<223> OTHER INFORMATION: Staple Strand

<400> SEQUENCE: 191
ttccagtaag cgtcatacat gtgacctgaa agcgtaagaa ta                     42

<210> SEQ ID NO 192
<211> LENGTH: 42
<212> TYPE: DNA
<213> ORGANISM: Artificial Sequence
<220> FEATURE:
<223> OTHER INFORMATION: Staple Strand

<400> SEQUENCE: 192
gattcaccag tcacacgacc aaaggtgaat tatcaccgtc ac                     42

<210> SEQ ID NO 193
<211> LENGTH: 42
<212> TYPE: DNA
<213> ORGANISM: Artificial Sequence
<220> FEATURE:

<223> OTHER INFORMATION: Staple Strand

<400> SEQUENCE: 193
caaaagggcg acattcaacc gaattcatca atataatcct ga					42

<210> SEQ ID NO 194
<211> LENGTH: 42
<212> TYPE: DNA
<213> ORGANISM: Artificial Sequence
<220> FEATURE:
<223> OTHER INFORMATION: Staple Strand

<400> SEQUENCE: 194
tttacaaaca attcgacaac tactttttca tgaggaagtt tc					42

<210> SEQ ID NO 195
<211> LENGTH: 42
<212> TYPE: DNA
<213> ORGANISM: Artificial Sequence
<220> FEATURE:
<223> OTHER INFORMATION: Staple Strand

<400> SEQUENCE: 195
caaccatcgc ccacgcataa caaagaacgt ggactccaac gt					42

<210> SEQ ID NO 196
<211> LENGTH: 42
<212> TYPE: DNA
<213> ORGANISM: Artificial Sequence
<220> FEATURE:
<223> OTHER INFORMATION: Staple Strand

<400> SEQUENCE: 196
gcagcaagcg gtccacgctg gggccggaaa cgtcaccaat ga					42

<210> SEQ ID NO 197
<211> LENGTH: 42
<212> TYPE: DNA
<213> ORGANISM: Artificial Sequence
<220> FEATURE:
<223> OTHER INFORMATION: Staple Strand

<400> SEQUENCE: 197
cgacttgagc catttgggaa taaagagtct gtccatcacg ca					42

<210> SEQ ID NO 198
<211> LENGTH: 42
<212> TYPE: DNA
<213> ORGANISM: Artificial Sequence
<220> FEATURE:
<223> OTHER INFORMATION: Staple Strand

<400> SEQUENCE: 198
tggttgcttt gacgagcacg tcttttgcgg gatcgtcacc ct					42

<210> SEQ ID NO 199
<211> LENGTH: 42
<212> TYPE: DNA
<213> ORGANISM: Artificial Sequence
<220> FEATURE:
<223> OTHER INFORMATION: Staple Strand

<400> SEQUENCE: 199
cttgcaggga gttaaaggcc gataacgtgc tttcctcgtt ag					42

```
<210> SEQ ID NO 200
<211> LENGTH: 42
<212> TYPE: DNA
<213> ORGANISM: Artificial Sequence
<220> FEATURE:
<223> OTHER INFORMATION: Staple Strand

<400> SEQUENCE: 200
aatcagagcg ggagctaaac accgtaacac tgagtttcgt ca                              42

<210> SEQ ID NO 201
<211> LENGTH: 42
<212> TYPE: DNA
<213> ORGANISM: Artificial Sequence
<220> FEATURE:
<223> OTHER INFORMATION: Staple Strand

<400> SEQUENCE: 201
ggaggtttag taccgccacc ctgagtaaca ttatcatttt gc                              42

<210> SEQ ID NO 202
<211> LENGTH: 42
<212> TYPE: DNA
<213> ORGANISM: Artificial Sequence
<220> FEATURE:
<223> OTHER INFORMATION: Staple Strand

<400> SEQUENCE: 202
acgttattaa ttttaaaagt ttcagaaccg ccaccctcag aa                              42

<210> SEQ ID NO 203
<211> LENGTH: 42
<212> TYPE: DNA
<213> ORGANISM: Artificial Sequence
<220> FEATURE:
<223> OTHER INFORMATION: Staple Strand

<400> SEQUENCE: 203
ccgccaccct cagagccacc agaatggcta ttagtcttta at                              42

<210> SEQ ID NO 204
<211> LENGTH: 42
<212> TYPE: DNA
<213> ORGANISM: Artificial Sequence
<220> FEATURE:
<223> OTHER INFORMATION: Staple Strand

<400> SEQUENCE: 204
cgtggcacag acaatatttt tccctcattt tcagggatag ca                              42

<210> SEQ ID NO 205
<211> LENGTH: 42
<212> TYPE: DNA
<213> ORGANISM: Artificial Sequence
<220> FEATURE:
<223> OTHER INFORMATION: Staple Strand

<400> SEQUENCE: 205
cagcagcgaa agacagcatc gacatcgcca ttaaaaatac cg                              42

<210> SEQ ID NO 206
<211> LENGTH: 42
<212> TYPE: DNA
<213> ORGANISM: Artificial Sequence
<220> FEATURE:
<223> OTHER INFORMATION: Staple Strand
```

<400> SEQUENCE: 206
gcgcgaactg atagccctaa agaacgaggg tagcaacggc ta                         42

<210> SEQ ID NO 207
<211> LENGTH: 42
<212> TYPE: DNA
<213> ORGANISM: Artificial Sequence
<220> FEATURE:
<223> OTHER INFORMATION: Staple Strand

<400> SEQUENCE: 207
agcccaatag gaacccatgt aggaggccga ttaaagggat tt                         42

<210> SEQ ID NO 208
<211> LENGTH: 42
<212> TYPE: DNA
<213> ORGANISM: Artificial Sequence
<220> FEATURE:
<223> OTHER INFORMATION: Staple Strand

<400> SEQUENCE: 208
atcaaaagaa tagcccgaga tgtagcattc cacagacagc cc                         42

<210> SEQ ID NO 209
<211> LENGTH: 42
<212> TYPE: DNA
<213> ORGANISM: Artificial Sequence
<220> FEATURE:
<223> OTHER INFORMATION: Staple Strand

<400> SEQUENCE: 209
ccagtacaaa ctacaacgcc tagggttgag tgttgttcca gt                         42

<210> SEQ ID NO 210
<211> LENGTH: 42
<212> TYPE: DNA
<213> ORGANISM: Artificial Sequence
<220> FEATURE:
<223> OTHER INFORMATION: Staple Strand

<400> SEQUENCE: 210
tagacaggaa cggtacgcca ggcgcagtct ctgaatttac cg                         42

<210> SEQ ID NO 211
<211> LENGTH: 42
<212> TYPE: DNA
<213> ORGANISM: Artificial Sequence
<220> FEATURE:
<223> OTHER INFORMATION: Staple Strand

<400> SEQUENCE: 211
aggtcagacg attggccttg aaatcggcaa atcccttat aa                          42

<210> SEQ ID NO 212
<211> LENGTH: 42
<212> TYPE: DNA
<213> ORGANISM: Artificial Sequence
<220> FEATURE:
<223> OTHER INFORMATION: Staple Strand

<400> SEQUENCE: 212
cctgtttgat ggtggttccg atattcacaa acaaataaat cc                         42

<210> SEQ ID NO 213
<211> LENGTH: 42

<212> TYPE: DNA
<213> ORGANISM: Artificial Sequence
<220> FEATURE:
<223> OTHER INFORMATION: Staple Strand

<400> SEQUENCE: 213
tcattaaagc cagaatggaa aaatcctgag aagtgttttt at                     42

<210> SEQ ID NO 214
<211> LENGTH: 42
<212> TYPE: DNA
<213> ORGANISM: Artificial Sequence
<220> FEATURE:
<223> OTHER INFORMATION: Staple Strand

<400> SEQUENCE: 214
ggaacaaaga aaccaccaga agggtcagtg ccttgagtaa ca                     42

<210> SEQ ID NO 215
<211> LENGTH: 42
<212> TYPE: DNA
<213> ORGANISM: Artificial Sequence
<220> FEATURE:
<223> OTHER INFORMATION: Staple Strand

<400> SEQUENCE: 215
tactggtaat aagttttaac gggagcggaa ttatcatcat at                     42

<210> SEQ ID NO 216
<211> LENGTH: 42
<212> TYPE: DNA
<213> ORGANISM: Artificial Sequence
<220> FEATURE:
<223> OTHER INFORMATION: Staple Strand

<400> SEQUENCE: 216
ccaacagaga tagaacccctt cgcttttgat gatacaggag tg                    42

<210> SEQ ID NO 217
<211> LENGTH: 42
<212> TYPE: DNA
<213> ORGANISM: Artificial Sequence
<220> FEATURE:
<223> OTHER INFORMATION: Staple Strand

<400> SEQUENCE: 217
aatcagtgag gccaccgagt atagagccag caaaatcacc ag                     42

<210> SEQ ID NO 218
<211> LENGTH: 42
<212> TYPE: DNA
<213> ORGANISM: Artificial Sequence
<220> FEATURE:
<223> OTHER INFORMATION: Staple Strand

<400> SEQUENCE: 218
tagcaccatt accattagca atttgcccca gcaggcgaaa at                     42

<210> SEQ ID NO 219
<211> LENGTH: 42
<212> TYPE: DNA
<213> ORGANISM: Artificial Sequence
<220> FEATURE:
<223> OTHER INFORMATION: Staple Strand

<400> SEQUENCE: 219
ttggaacaag agtccactat tcgatatatt cggtcgctga gg    42

<210> SEQ ID NO 220
<211> LENGTH: 42
<212> TYPE: DNA
<213> ORGANISM: Artificial Sequence
<220> FEATURE:
<223> OTHER INFORMATION: Staple Strand

<400> SEQUENCE: 220
cagaggcttt gaggactaaa gcgtattaaa tcctttgccc ga    42

<210> SEQ ID NO 221
<211> LENGTH: 42
<212> TYPE: DNA
<213> ORGANISM: Artificial Sequence
<220> FEATURE:
<223> OTHER INFORMATION: Staple Strand

<400> SEQUENCE: 221
tcctgattat cagatgatgg cattgaggga gggaaggtaa at    42

<210> SEQ ID NO 222
<211> LENGTH: 42
<212> TYPE: DNA
<213> ORGANISM: Artificial Sequence
<220> FEATURE:
<223> OTHER INFORMATION: Staple Strand

<400> SEQUENCE: 222
attgacggaa attattcatt agtaataaaa gggacattct gg    42

<210> SEQ ID NO 223
<211> LENGTH: 42
<212> TYPE: DNA
<213> ORGANISM: Artificial Sequence
<220> FEATURE:
<223> OTHER INFORMATION: Staple Strand

<400> SEQUENCE: 223
tttgccagag ggggtaatag tgtgccacgc tgagagccag ca    42

<210> SEQ ID NO 224
<211> LENGTH: 42
<212> TYPE: DNA
<213> ORGANISM: Artificial Sequence
<220> FEATURE:
<223> OTHER INFORMATION: Staple Strand

<400> SEQUENCE: 224
aacgaaccac cagcagaaga tatgaacggt gtacagacca gg    42

<210> SEQ ID NO 225
<211> LENGTH: 42
<212> TYPE: DNA
<213> ORGANISM: Artificial Sequence
<220> FEATURE:
<223> OTHER INFORMATION: Staple Strand

<400> SEQUENCE: 225
cggaacgagg cgcagacggt cgaggattta gaagtattag ac    42

<210> SEQ ID NO 226
<211> LENGTH: 42
<212> TYPE: DNA
<213> ORGANISM: Artificial Sequence
<220> FEATURE:
<223> OTHER INFORMATION: Staple Strand

<400> SEQUENCE: 226
caaagggcga aaaccgtct aatcaacgta acaaagctgc tc                42

<210> SEQ ID NO 227
<211> LENGTH: 42
<212> TYPE: DNA
<213> ORGANISM: Artificial Sequence
<220> FEATURE:
<223> OTHER INFORMATION: Staple Strand

<400> SEQUENCE: 227
cgcataggct ggctgacctt cgccgctaca gggcgcgtac ta                42

<210> SEQ ID NO 228
<211> LENGTH: 42
<212> TYPE: DNA
<213> ORGANISM: Artificial Sequence
<220> FEATURE:
<223> OTHER INFORMATION: Staple Strand

<400> SEQUENCE: 228
cgtggcgaga aggaaggga aatatgcaac taaagtacgg tg                42

<210> SEQ ID NO 229
<211> LENGTH: 42
<212> TYPE: DNA
<213> ORGANISM: Artificial Sequence
<220> FEATURE:
<223> OTHER INFORMATION: Staple Strand

<400> SEQUENCE: 229
aggattagag agtaccttta agaaaggaat tgaggaaggt ta                42

<210> SEQ ID NO 230
<211> LENGTH: 42
<212> TYPE: DNA
<213> ORGANISM: Artificial Sequence
<220> FEATURE:
<223> OTHER INFORMATION: Staple Strand

<400> SEQUENCE: 230
tcagttggca aatcaacagt tttgctcctt ttgataagag gt                42

<210> SEQ ID NO 231
<211> LENGTH: 42
<212> TYPE: DNA
<213> ORGANISM: Artificial Sequence
<220> FEATURE:
<223> OTHER INFORMATION: Staple Strand

<400> SEQUENCE: 231 cattttgcg gatggcttag atcaccttgc tgaacctcaa at                 42

<210> SEQ ID NO 232
<211> LENGTH: 42
<212> TYPE: DNA
<213> ORGANISM: Artificial Sequence
<220> FEATURE:
<223> OTHER INFORMATION: Staple Strand

<400> SEQUENCE: 232
gcaaatgaaa aatctaaagc agcttaattg ctgaatataa tg                42

<210> SEQ ID NO 233
<211> LENGTH: 42
<212> TYPE: DNA
<213> ORGANISM: Artificial Sequence
<220> FEATURE:
<223> OTHER INFORMATION: Staple Strand

<400> SEQUENCE: 233
ctgtagctca acatgtttta agaaagcgaa aggagcgggc gc        42

<210> SEQ ID NO 234
<211> LENGTH: 42
<212> TYPE: DNA
<213> ORGANISM: Artificial Sequence
<220> FEATURE:
<223> OTHER INFORMATION: Staple Strand

<400> SEQUENCE: 234
taaagcacta atcggaacc caacagttga ttcccaattc tg         42

<210> SEQ ID NO 235
<211> LENGTH: 42
<212> TYPE: DNA
<213> ORGANISM: Artificial Sequence
<220> FEATURE:
<223> OTHER INFORMATION: Staple Strand

<400> SEQUENCE: 235
tctggaagtt tcattccata ttaaagggag cccccgattt ag        42

<210> SEQ ID NO 236
<211> LENGTH: 42
<212> TYPE: DNA
<213> ORGANISM: Artificial Sequence
<220> FEATURE:
<223> OTHER INFORMATION: Staple Strand

<400> SEQUENCE: 236
tagggcgctg gcaagtgtag cagaggcttt tgcaaaagaa gt        42

<210> SEQ ID NO 237
<211> LENGTH: 42
<212> TYPE: DNA
<213> ORGANISM: Artificial Sequence
<220> FEATURE:
<223> OTHER INFORMATION: Staple Strand

<400> SEQUENCE: 237
catagtaaga gcaacactat cttttttggg gtcgaggtgc cg        42

<210> SEQ ID NO 238
<211> LENGTH: 42
<212> TYPE: DNA
<213> ORGANISM: Artificial Sequence
<220> FEATURE:
<223> OTHER INFORMATION: Staple Strand

<400> SEQUENCE: 238
tgaaccatca cccaaatcaa gataaccctc gtttaccaga cg        42

<210> SEQ ID NO 239
<211> LENGTH: 42
<212> TYPE: DNA
<213> ORGANISM: Artificial Sequence
<220> FEATURE:
<223> OTHER INFORMATION: Staple Strand

```
<400> SEQUENCE: 239
acgataaaaa ccaaaatagc gggtcacgct gcgcgtaacc ac                              42

<210> SEQ ID NO 240
<211> LENGTH: 42
<212> TYPE: DNA
<213> ORGANISM: Artificial Sequence
<220> FEATURE:
<223> OTHER INFORMATION: Staple Strand

<400> SEQUENCE: 240
tctaaaatat ctttaggagc aataaatatt cattgaatcc cc                              42

<210> SEQ ID NO 241
<211> LENGTH: 42
<212> TYPE: DNA
<213> ORGANISM: Artificial Sequence
<220> FEATURE:
<223> OTHER INFORMATION: Staple Strand

<400> SEQUENCE: 241
gtccaatact gcggaatcgt cctaacaact aatagattag ag                              42

<210> SEQ ID NO 242
<211> LENGTH: 42
<212> TYPE: DNA
<213> ORGANISM: Artificial Sequence
<220> FEATURE:
<223> OTHER INFORMATION: Staple Strand

<400> SEQUENCE: 242
gtattaacac cgcctgcaac aaaaatgttt agactggata gc                              42

<210> SEQ ID NO 243
<211> LENGTH: 42
<212> TYPE: DNA
<213> ORGANISM: Artificial Sequence
<220> FEATURE:
<223> OTHER INFORMATION: Staple Strand

<400> SEQUENCE: 243
cacacccgcc gcgcttaatg catcaagagt aatcttgaca ag                              42

<210> SEQ ID NO 244
<211> LENGTH: 42
<212> TYPE: DNA
<213> ORGANISM: Artificial Sequence
<220> FEATURE:
<223> OTHER INFORMATION: Staple Strand

<400> SEQUENCE: 244
aaccggatat tcattaccca atcagggcga tggcccacta cg                              42

<210> SEQ ID NO 245
<211> LENGTH: 42
<212> TYPE: DNA
<213> ORGANISM: Artificial Sequence
<220> FEATURE:
<223> OTHER INFORMATION: Staple Strand

<400> SEQUENCE: 245
ccgtcaatag ataatacatt taatcataag ggaaccgaac tg                              42

<210> SEQ ID NO 246
```

```
<211> LENGTH: 42
<212> TYPE: DNA
<213> ORGANISM: Artificial Sequence
<220> FEATURE:
<223> OTHER INFORMATION: Staple Strand

<400> SEQUENCE: 246
accaactttg aaagaggaca gaaaacagag gtgaggcggt ca                              42

<210> SEQ ID NO 247
<211> LENGTH: 42
<212> TYPE: DNA
<213> ORGANISM: Artificial Sequence
<220> FEATURE:
<223> OTHER INFORMATION: Staple Strand

<400> SEQUENCE: 247
atcaacaata gataagtcct gtgtccagac gacgacaata aa                              42

<210> SEQ ID NO 248
<211> LENGTH: 42
<212> TYPE: DNA
<213> ORGANISM: Artificial Sequence
<220> FEATURE:
<223> OTHER INFORMATION: Staple Strand

<400> SEQUENCE: 248
gcagaggcat tttcgagcca ggtatgttag caaacgtaga aa                              42

<210> SEQ ID NO 249
<211> LENGTH: 42
<212> TYPE: DNA
<213> ORGANISM: Artificial Sequence
<220> FEATURE:
<223> OTHER INFORMATION: Staple Strand

<400> SEQUENCE: 249
aggaaacgca ataataacgg attgctttga ataccaagtt ac                              42

<210> SEQ ID NO 250
<211> LENGTH: 42
<212> TYPE: DNA
<213> ORGANISM: Artificial Sequence
<220> FEATURE:
<223> OTHER INFORMATION: Staple Strand

<400> SEQUENCE: 250
gtcagatgaa tatacagtaa caaaccaatc aataatcggc tg                              42

<210> SEQ ID NO 251
<211> LENGTH: 42
<212> TYPE: DNA
<213> ORGANISM: Artificial Sequence
<220> FEATURE:
<223> OTHER INFORMATION: Staple Strand

<400> SEQUENCE: 251
tcctaattta cgagcatgta gagtaccttt tacatcggga ga                              42

<210> SEQ ID NO 252
<211> LENGTH: 42
<212> TYPE: DNA
<213> ORGANISM: Artificial Sequence
<220> FEATURE:
<223> OTHER INFORMATION: Staple Strand

<400> SEQUENCE: 252
```
aacaataacg gattcgcctg aatacccaaa agaactggca tg    42

<210> SEQ ID NO 253
<211> LENGTH: 42
<212> TYPE: DNA
<213> ORGANISM: Artificial Sequence
<220> FEATURE:
<223> OTHER INFORMATION: Staple Strand

<400> SEQUENCE: 253
attaagactc cttattacgc ataataagag aatataaagt ac    42

<210> SEQ ID NO 254
<211> LENGTH: 42
<212> TYPE: DNA
<213> ORGANISM: Artificial Sequence
<220> FEATURE:
<223> OTHER INFORMATION: Staple Strand

<400> SEQUENCE: 254
cgacaaaagg taaagtaatt caacaagaaa aataatatcc ca    42

<210> SEQ ID NO 255
<211> LENGTH: 42
<212> TYPE: DNA
<213> ORGANISM: Artificial Sequence
<220> FEATURE:
<223> OTHER INFORMATION: Staple Strand

<400> SEQUENCE: 255
cattaaacgg gtaaaatacg ttgagtgaat aaccttgctt ct    42

<210> SEQ ID NO 256
<211> LENGTH: 42
<212> TYPE: DNA
<213> ORGANISM: Artificial Sequence
<220> FEATURE:
<223> OTHER INFORMATION: Staple Strand

<400> SEQUENCE: 256
aaaatcgcgc agaggcgaat tatggtttac cagcgccaaa ga    42

<210> SEQ ID NO 257
<211> LENGTH: 42
<212> TYPE: DNA
<213> ORGANISM: Artificial Sequence
<220> FEATURE:
<223> OTHER INFORMATION: Staple Strand

<400> SEQUENCE: 257 ataaagaaa cgcaaagaca ccaacgccaa catgtaattt ag    42

<210> SEQ ID NO 258
<211> LENGTH: 42
<212> TYPE: DNA
<213> ORGANISM: Artificial Sequence
<220> FEATURE:
<223> OTHER INFORMATION: Staple Strand

<400> SEQUENCE: 258
gtgataaata aggcgttaaa tagaatacac taaaacactc at    42

<210> SEQ ID NO 259
<211> LENGTH: 42
<212> TYPE: DNA

<213> ORGANISM: Artificial Sequence
<220> FEATURE:
<223> OTHER INFORMATION: Staple Strand

<400> SEQUENCE: 259
acctaaaacg aaagaggcaa aaagaataaa caccggaatc at        42

<210> SEQ ID NO 260
<211> LENGTH: 42
<212> TYPE: DNA
<213> ORGANISM: Artificial Sequence
<220> FEATURE:
<223> OTHER INFORMATION: Staple Strand

<400> SEQUENCE: 260
aattactaga aaaagcctgt tggataagtg ccgtcgagag gg        42

<210> SEQ ID NO 261
<211> LENGTH: 42
<212> TYPE: DNA
<213> ORGANISM: Artificial Sequence
<220> FEATURE:
<223> OTHER INFORMATION: Staple Strand

<400> SEQUENCE: 261
gggttttgct cagtaccagg ctagtatcat atgcgttata ca        42

<210> SEQ ID NO 262
<211> LENGTH: 42
<212> TYPE: DNA
<213> ORGANISM: Artificial Sequence
<220> FEATURE:
<223> OTHER INFORMATION: Staple Strand

<400> SEQUENCE: 262
tacatttaac aatttcattt gataggtgta tcaccgtact ca        42

<210> SEQ ID NO 263
<211> LENGTH: 42
<212> TYPE: DNA
<213> ORGANISM: Artificial Sequence
<220> FEATURE:
<223> OTHER INFORMATION: Staple Strand

<400> SEQUENCE: 263
ttgatataag tatagcccgg aaattacctt ttttaatgga aa        42

<210> SEQ ID NO 264
<211> LENGTH: 42
<212> TYPE: DNA
<213> ORGANISM: Artificial Sequence
<220> FEATURE:
<223> OTHER INFORMATION: Staple Strand

<400> SEQUENCE: 264
aattcttacc agtataaagc cgtattaaga ggctgagact cc        42

<210> SEQ ID NO 265
<211> LENGTH: 42
<212> TYPE: DNA
<213> ORGANISM: Artificial Sequence
<220> FEATURE:
<223> OTHER INFORMATION: Staple Strand

<400> SEQUENCE: 265
gtgcccgtat aaacagttaa tcatcaagaa aacaaaatta at        42

<210> SEQ ID NO 266
<211> LENGTH: 42
<212> TYPE: DNA
<213> ORGANISM: Artificial Sequence
<220> FEATURE:
<223> OTHER INFORMATION: Staple Strand

<400> SEQUENCE: 266
aaaagaagat gatgaaacaa agcccctgc ctatttcgga ac        42

<210> SEQ ID NO 267
<211> LENGTH: 42
<212> TYPE: DNA
<213> ORGANISM: Artificial Sequence
<220> FEATURE:
<223> OTHER INFORMATION: Staple Strand

<400> SEQUENCE: 267
ctattattct gaaacatgaa aaacgctcaa cagtagggct ta        42

<210> SEQ ID NO 268
<211> LENGTH: 42
<212> TYPE: DNA
<213> ORGANISM: Artificial Sequence
<220> FEATURE:
<223> OTHER INFORMATION: Staple Strand

<400> SEQUENCE: 268
attgagaatc gccatattta acacggaata agtttatttt gt        42

<210> SEQ ID NO 269
<211> LENGTH: 42
<212> TYPE: DNA
<213> ORGANISM: Artificial Sequence
<220> FEATURE:
<223> OTHER INFORMATION: Staple Strand

<400> SEQUENCE: 269
cacaatcaat agaaaattca tattcatttc aattacctga gc        42

<210> SEQ ID NO 270
<211> LENGTH: 42
<212> TYPE: DNA
<213> ORGANISM: Artificial Sequence
<220> FEATURE:
<223> OTHER INFORMATION: Staple Strand

<400> SEQUENCE: 270
cagtacataa atcaatatat gaatgccact acgaaggcac ca        42

<210> SEQ ID NO 271
<211> LENGTH: 42
<212> TYPE: DNA
<213> ORGANISM: Artificial Sequence
<220> FEATURE:
<223> OTHER INFORMATION: Staple Strand

<400> SEQUENCE: 271
gtaaatcgtc gctattaatt aacctgctcc atgttactta gc        42

<210> SEQ ID NO 272
<211> LENGTH: 42
<212> TYPE: DNA
<213> ORGANISM: Artificial Sequence
<220> FEATURE:

<223> OTHER INFORMATION: Staple Strand

<400> SEQUENCE: 272
agcgcgaaac aaagtacaac gatggtttga ataccgacc gt                42

<210> SEQ ID NO 273
<211> LENGTH: 42
<212> TYPE: DNA
<213> ORGANISM: Artificial Sequence
<220> FEATURE:
<223> OTHER INFORMATION: Staple Strand

<400> SEQUENCE: 273
tataactata tgtaaatgct gcaaatatcg cgttttaatt cg                42

<210> SEQ ID NO 274
<211> LENGTH: 42
<212> TYPE: DNA
<213> ORGANISM: Artificial Sequence
<220> FEATURE:
<223> OTHER INFORMATION: Staple Strand

<400> SEQUENCE: 274
aagaggaagc ccgaaagact tatgcaaatc caatcgcaag ac                42

<210> SEQ ID NO 275
<211> LENGTH: 42
<212> TYPE: DNA
<213> ORGANISM: Artificial Sequence
<220> FEATURE:
<223> OTHER INFORMATION: Staple Strand

<400> SEQUENCE: 275
tagtgaattt atcaaaatca tggaagcaaa ctccaacagg tc                42

<210> SEQ ID NO 276
<211> LENGTH: 42
<212> TYPE: DNA
<213> ORGANISM: Artificial Sequence
<220> FEATURE:
<223> OTHER INFORMATION: Staple Strand

<400> SEQUENCE: 276
agcttcaaag cgaaccagac caggtctgag agactacctt tt                42

<210> SEQ ID NO 277
<211> LENGTH: 42
<212> TYPE: DNA
<213> ORGANISM: Artificial Sequence
<220> FEATURE:
<223> OTHER INFORMATION: Staple Strand

<400> SEQUENCE: 277
aaagaacgcg agaaaacttt tctgactatt atagtcagaa gc                42

<210> SEQ ID NO 278
<211> LENGTH: 42
<212> TYPE: DNA
<213> ORGANISM: Artificial Sequence
<220> FEATURE:
<223> OTHER INFORMATION: Staple Strand

<400> SEQUENCE: 278
ctcaaatgct ttaaacagtt ctaagacgct gagaagagtc aa                42

```
<210> SEQ ID NO 279
<211> LENGTH: 42
<212> TYPE: DNA
<213> ORGANISM: Artificial Sequence
<220> FEATURE:
<223> OTHER INFORMATION: Staple Strand

<400> SEQUENCE: 279
aaacatagcg atagcttaga tagaaaacga gaatgaccat aa                              42

<210> SEQ ID NO 280
<211> LENGTH: 42
<212> TYPE: DNA
<213> ORGANISM: Artificial Sequence
<220> FEATURE:
<223> OTHER INFORMATION: Staple Strand

<400> SEQUENCE: 280
atcaaaaatc aggtctttac ctcaaatata ttttagttaa tt                              42

<210> SEQ ID NO 281
<211> LENGTH: 42
<212> TYPE: DNA
<213> ORGANISM: Artificial Sequence
<220> FEATURE:
<223> OTHER INFORMATION: Staple Strand

<400> SEQUENCE: 281
tcatcttctg acctaaattt agagatttgt atcatcgcct ga                              42

<210> SEQ ID NO 282
<211> LENGTH: 42
<212> TYPE: DNA
<213> ORGANISM: Artificial Sequence
<220> FEATURE:
<223> OTHER INFORMATION: Staple Strand

<400> SEQUENCE: 282
taaattgtgt cgaaatccgc gatttteect tagaatcctt ga                              42
```

What is claimed is:

1. A composition comprising
a plurality of immobile Holliday junction analogs linked together in a layered square frame having at least two layers in which the DNA helices which lie on opposite sides of the Holliday junction also lie in the same plane, and wherein said plurality of immobile Holliday junction analogs are linked together with a central strand of single-stranded DNA within said square frame.

2. The composition of claim 1, wherein said plurality of immobile Holliday junction analogs are linked together in a square frame having at least three layers.

3. The composition of claim 1, wherein said plurality of immobile Holliday junction analogs are linked together in a square frame having at least four layers.

4. The composition of claim 1, wherein said single stranded DNA comprises M13mp18 DNA.

5. The composition of claim 2, wherein the square frame having at least three layers comprises a lattice defined by the lengths of said lattice, and the interstitial space confined by the lattice defines a cavity;
wherein the lattice comprises at least three double-stranded DNA strands, each of which has an independent length.

6. The composition of claim 5, wherein the cavity size length of the double-stranded DNA strands is from 21 nt to 63 nt.

7. The composition of claim 3, wherein the square frame having at least four layers, comprises a lattice defined by the lengths of said lattice, and the interstitial space confined by the lattice defines a cavity,
wherein the lattice comprises at least three separate lengths of double-stranded DNA.

8. The composition of claim 7, wherein the length of the double-stranded DNA strands is from 21 nt to 63 nt.

* * * * *